US008758796B2

(12) United States Patent
Ameer et al.

(10) Patent No.: US 8,758,796 B2
(45) Date of Patent: Jun. 24, 2014

(54) FUNCTIONALIZING IMPLANTABLE DEVICES WITH A POLY (DIOL CITRATE) POLYMER

(71) Applicant: Northwestern University, Evanston, IL (US)

(72) Inventors: Guillermo Ameer, Chicago, IL (US); Jian Yang, Arlington, TX (US); Melina Kibbe, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/848,339

(22) Filed: Mar. 21, 2013

(65) Prior Publication Data

US 2013/0287682 A1 Oct. 31, 2013

Related U.S. Application Data

(63) Continuation of application No. 13/311,853, filed on Dec. 6, 2011, now Pat. No. 8,404,264, which is a continuation of application No. 11/704,039, filed on Feb. 8, 2007, now abandoned.

(60) Provisional application No. 60/771,348, filed on Feb. 8, 2006.

(51) Int. Cl.
*A61F 2/00* (2006.01)

(52) U.S. Cl.
USPC ............................ 424/423; 424/422; 424/424

(58) Field of Classification Search
CPC ........ A61L 31/16; A61L 31/148; A61L 31/08
See application file for complete search history.

(56) References Cited

U.S. PATENT DOCUMENTS

| | | | |
|---|---|---|---|
| 4,352,883 A | 10/1982 | Lim | |
| 4,409,331 A | 10/1983 | Lim | |
| 4,475,972 A | 10/1984 | Wong | |
| 5,874,500 A | 2/1999 | Rhee et al. | |
| 5,891,076 A | 4/1999 | Fabo | |
| 5,993,843 A | 11/1999 | Sakurada et al. | |
| 6,051,648 A | 4/2000 | Rhee et al. | |
| 6,106,558 A | 8/2000 | Picha | |
| 6,166,130 A | 12/2000 | Rhee et al. | |
| 6,221,109 B1 | 4/2001 | Geistlich et al. | |
| 6,284,941 B1 | 9/2001 | Cox et al. | |
| 6,323,278 B2 | 11/2001 | Rhee et al. | |
| 6,461,640 B1 | 10/2002 | Hubbell et al. | |
| 6,531,146 B2 | 3/2003 | Calhoun et al. | |
| 6,548,728 B1 | 4/2003 | Faries, Jr. et al. | |
| 6,572,878 B1 | 6/2003 | Blaine | |
| 6,620,203 B2 | 9/2003 | Atala | |
| 2004/0137033 A1 | 7/2004 | Calhoun et al. | |
| 2004/0253203 A1 | 12/2004 | Hossainy et al. | |
| 2005/0063939 A1 | 3/2005 | Ameer et al. | |
| 2005/0288481 A1 | 12/2005 | Desnoyer et al. | |
| 2007/0071790 A1 | 3/2007 | Ameer et al. | |

FOREIGN PATENT DOCUMENTS

WO 2005/028631 3/2005

OTHER PUBLICATIONS

Akers, The Effect of Carbon Coating and Porosity on Early Patency of Expanded Polytetrafluoroethylene Grafts: An Experimental Study, J. Vase. Sur,q. 18:10-15 (1993).
Akpalu et al., Multivariable structural characterization of semicrystalline polymer blends by small-angle light scattering. J. Polym. Sci. 8 Polym. Phys., 40: 2714-27 (2002).
Arshady, Preparation of Biodegradable Microspheres and Microcapsules: 2.Polyactides and Related Polyesters, Journal of Controlled Release, 17:1-21 (1991 ).
Asahara, Isolation of Putative Progenitor Endothelial Cells for Angiogenesis, Science, 275:964-967 (1997).
Barlett et al., Measurement of particle size distribution in multilayered skin phantoms using polarized light spectroscopy. Physical Review E., 65: 031906-1-031906-8 (2002).
Bezuidenhout, Vascular Grafts in Wnek, ed., Encyclopedia of Biomaterials and Biomedical Engineering, Marcel Dekker (2004 ).
Bordenave et al., Clinical performance of vascular grafts lined with endothelial cells. Endothelium, 6: 267-75 (1999).
Bos et al., Small-diameter vascular graft prostheses: Current status. Arch. Physiol. Biochem., 106: 100-15 (1998).
Carnagey et al., Rapid endothelialization of Photo Fix natural biomaterial vascular grafts. J. Biomed. Mater. Res. Part 8: Appl. Biomater., 65B: 171-9 (2003).
Cascone, Collagen and Hyaluronic Acid Based Polymeric Blends as Drug Delivery Systems for the Release of Physiological Concentrations of Growth Hormone, Journal of Materials Science: Materials in Medicine, 5:770 (1994).
Chiba et al., Mechanical responses of the periodontal ligament in the transverse section of the rat mandibular incisor at various velocities of loading in vitro. Biomech., 26: 561-70 (1993).
Chen, Phosphorylcholine Coating of ePTFE Reduces Platelet Deposition and Neointimal Hyperplasia in Arteriovenous Grafts, J. Surg. Res., 77:119-125 (1998).
Chen, Surface Modification of Biaxially Expanded Poly(tetrafluoroethylene) by Plasma Polymerization of Ethylene, Surface and Coating Technology, 176:148-156 (2004).
Consigny, Endothelial cell seeding on prosthetic surfaces. J. Long Term Eft. Med. Implants, 10: 79-95 (2000).
Dekker et al., Adhesion of endothelial cells and adsorption of serum proteins on gas plasmatreated polytetrafluoroethylene. Biomaterials, 12: 130-8 ( 1991 ).
Dunn, Synthesis of N-(aminoalkyl) Chitosan for Microcapsules, Journal of Applied Polymer Science, 50:353-365 (1993).

(Continued)

*Primary Examiner* — James Rogers
(74) *Attorney, Agent, or Firm* — Casimir Jones, S.C.

(57) ABSTRACT

The present invention is directed to a novel poly(diol citrates)-based coating for implantable devices. More specifically, the specification describes methods and compositions for making and using implantable devices coated with citric acid copolymers or citric acid copolymers impregnated with therapeutic compositions and/or cells.

14 Claims, 10 Drawing Sheets

(56) References Cited

OTHER PUBLICATIONS

Freshney, Culture of Animal Cells: A Manual of Basic Technique, 2d ed., New York: A.R. Liss, Inc., 9:107-126; and 11-12:137-168 (1987).
Gospodarowicz, Extracellular Matrix and Control of Proliferation of Vascular Endothelial Cells, J. Clin. Invest., 65:1351-1364 (1980).
Greenwald et al., Improving vascular grafts: The importance of mechanical and haemodynamic properties. J. Pathol., 190: 292-9 (2000).
Greisser et al., Growth of human cells on plasma polymers: Putative role of amine and amide groups. J. Biomater. Sci. Polymer Edn., 5: 531-54 (1994).
Griffith, Polymeric biomaterials. Acta Mater., 48: 263-77 (2000).
Guan, Biodegradable Poly( ether ester urethane) Urea Elastomers Based on Poly (ether ester) Triblock Copolymers and Putrescine: Synthesis, Characterization and Cytocompatibility, Biomaterials, 25:85-96 (2004 ).
Guldberg, Consideration of mechanical factors. Ann. N. Y. Acad. Sci., 961:312-4 (2002).
Holland, Polymers for Biodegradable Medical Devices. 1. The Potential of Polyesters as Controlled Macromolecular Release Systems, Journal of Controlled Release, 4:155-180 (1986).
Kakisis, Artificial Blood Vessel: The Holy Grail of Peripheral Vascular Surgery, J. Vase. Surg., 41 :349-354 (2005).
Kang, A Novel Biodegradable Elastomer for Cartilage Tissue Engineering, J. Biomed. Mater. Res., 77(2):331-339 (2006).
Kannan, Current Status of Prosthetic Bypass Grafts: A Review, J. Biomed. Mater. Res. Part B: Appl. Biomater., 74B:570-581 (2005).
Kim et al., Optimizing seeding and culture methods to engineer smooth muscle tissue on biodegradable polymer matrices. Biotechnol. Bioenq., 57: 46-54 (1998).
Kim et al., Simultaneous measurement of angular and spectral properties of light scattering for characterization of tissue microarchitecture and its alteration in early precancer. J. Set. Top. Quant. Elect., 9: 243-56 (2003).
Kweon et al., A novel degradable polycaprolactone networks for tissue engineering. Biomaterials, 24: 801-8 (2003).
Langer et al., Tissue engineering. Science, 260: 920-6 (1993).
Lee et al., Strain rate effects on tensile failure properties of the common carotid artery and jugular veins of ferrets. J. Biomech., 25:925-7 (1992).
L'Heureux, A Completely Biological Tissue-Engineered Human Blood Vessel, FASEB J., 12:47-56 (1998).
Li, Immobilization of Human Thrombomodulin to Expeander Polytetrafluoroethylene, Journal of Surgical Research, 104:200-208 (2002).
Lin, Small-caliber Heparin-coated ePTFE Grafts Reduce Platelet Deposition and Neointimal Hyperplasia in a Baboon Model, J. Vase. Surg., 39:1322-1328 (2004).
Lisowski et al., Crystallization behavior of poly( ethylene oxide) and its blends using timeresolved wide- and small-angle x-ray scattering. Macromolecules, 33: 4842-9 (2000).
Misof et al., A new molecular model for collagen elasticity based on synchrotron x-ray scattering evidence. Biophys. J., 72: 1376-81 (1997).
Miyazaki, Drug Release from Oral Mucosal Adhesive Tablets of Chitosan and Sodium Alginate, International Journal of Pharmaceutics, 118:257-263 (1995).
Nerem, Vascular Tissue Engineering, Annu. Rev. Biomed. Eng., 3:225-243 (2001 ).
Niklason, Advances in Tissue Engineering of Blood Vessels and Other Tissues, Transpl. Immunol., 5:303-306 (1997).
Niklason, Functional Arteries Grown in Vitro, Science, 284:489-493 (1999).
Noh, Chemical Modification and Photograft Polymerization Upon Expanded Poly(tetrafluoroethylene), J. Biomater. Sci. Polymer. Edn., 9:407-426 (1998).
Peichev, Expression of VEGFR-2 and AC133 by Circulating Human CD34(+) Cells Identifies a Population of Functional Endothelial Precursors, Blood, 95:952-958 (2000).
Pitt, The Controlled Parenteral Delivery of Polypeptides and Proteins, International Journal of Pharmaceutics, 59:173-197 (1990).
Principles of Polymeriation by Odian, 3rd Ed., pp. 1-2 (1993).
Salacinski, Cellular Engineering of Vascular Bypass Grafts: Role of Chemical Coatings for EnhancinQ Endothelial Cell Attachment, Med. Bioi. Eng. Comput., 39:609-618 (2001 ).
Seifalian, Improving the Clinical Patency of Prosthetic Vascular and Coronary Bypass Grafts: The Role of Seeding and Tissue Engineering, Artif. Organs, 26:307-320 (2002).
Shi, Evidence for Circulating Bone Marrow-derived Endothelial Cells, Blood, 92:362-367 (1998).
Shiraishi, Controlled-release Preparation of Indomethacin Using Calcium Alginate Gel, Bioi. Pharm. Bull. 16:1164-1168 (1993).
Szuromi et al., Preparation and analysis of cross-linked copolymers. Macromolecules, 33: 3993-8 (2000).
Tamada, Simple Method for Platelet Counting, Biomaterials, 16:259-261 (1995).
Teebken, Tissue Engineering of Small Diameter Vascular Grafts, Eur. J. Vase. Endovasc. Surg., 23:475-485 (2002).
Thacharodi, Collagen-chitosan Composite Membranes for Controlled Release of Propranolol Hydrochloride, International Journal of Pharmaceutics, 120:115-118 (1995).
Tiwari, New Prostheses for Use in Bypass Grafts with Special Emphasis on Polyurethanes, Cardiovascular Surgery, 10:191-197 (2002).
Tseng, Effects of Amide and Amine Plasma-treated ePTFE Vascular Grafts on Endothelial Cell Lining in an Artificial Circulatory System, J. Biomed. Mater. Res., 42:188-198 (1998).
Tsuchida, Modified Polytetrafluoroethylene: Indium 111-labeled Platelet Deposition on Carbon-lined and High-porosity Polytetrafluoroethylene Grafts, J. Vase. Surg., 16:649-650 (1992).
van der Zijpp, Endothelialization of Small-Diameter Vascular Prostheses, Arch. Physiol. Biochem., 111 :415-427 (2003).
van Wachem et al., Interation of cultured human endothelial cells with polymeric surfaces of different wettabilities. Biomaterials, 6: 403-8 (1985).
van Zanten et al., Phosphatidylcholine vesicle diameter, molecular weight and wall thickness determined by static light scattering. J. Colloid Interface Sci., 165: 512-8 (1994).
Vega et al., Latex particle size distribution by dynamic light scattering: Novel data processing for multiangle measurements. J. Colloid Interface Sci., 261: 74-81 (2003).
Vlodavsky, Endothelial Cell-derived Basic Fibroblast Growth Factor: Synthesis and Deposition into Subendothelial Extracellular Matrix, Proc. Nat/. Acad. Sci. USA, 84:2292-2296 (1987).
Wan, Cell Adhesion on Gaseous Plasma Modified Poly(L-lactide) Surface Under Shear Stress Field, Biomaterials, 24: 3757-3764 (2003).
Wang et al., A tough biodegradable elastomer. Nat. Biotech., 20: 602-6 (2002).
Wu et al., Preliminary report on microencapsulated islet transplantation in experimental diabetes mellitus in China. Int. J. Pancreatol., 3:91-100 (1988).
Xue et al., Biomaterial in the development and future of vascular grafts. J. Vas. Surg., 37:472-80 (2003).
Yamashita, Flk1-positive Cells Derived from Embryonic Stem Cells Serve as Vascular Progenitors. Nature, 408:92-96 (2000).
Yang, Biodegradable Elastomeric Polymers for Tissue Engineering, in Mallapragada, ed., C44 Handbook of Biodegradable Polymeric Materials and Their Applications, American Scientific Publishers, 191-232 (2005).
Yang, Enhanced Cell Affinity of Poly (D,L-lactide) by Combining Plasma Treatment with Collagen Anchorage, Biomaterials, 23:2607-2614 (2002).
Yang, Fabrication and Surface Modificationof Macroporous Poly (L-lactic acid) and Poly (LC46 lactic-co-glycolic acid) (70/30) Cells Scaffold for Human Skin Fibroblast Cells Culture, J. Biomed. Mater. Res., 62:438-446 (2002).

(56) References Cited

OTHER PUBLICATIONS

Yang, Improving Cell Affinity of Poly(D,L-lactide) Film Modified by Anhydrous Ammonia Plasma Treatment, Polym. Adv. Techno/., 13:220-226 (2002).

Yang, Novel Citric Acid-based Biodegradable Elastomers for Tissue Engineering, Adv. Mater., 16:511-516 (2004).

Yang, Plasma-treated, Collagen-anchored Polylactones: Its Cell Affinity Evaluation Under Shear or Shear-Free Conditions, J. Biomed. Mater. Res. 67:1139-1147 (2003).

Yang, Synthesis and Evaluation of Poly(diol citrates) Biodegradable Elastomers, Biomaterials, 27(9):1889-98 (2006).

Ziegler et al., Tissue engineering a blood vessel: Regulation of vascular biology by mechanical stresses. J. Cell Biochem., 56: 204-9 (1994).

Zhang, Biocompatibility Evaluation of ePTFE Membrane Modified with PEG in Atmospheric Pressure Glow Discharge, J. Biomed. Mater. Res., 60:502-509 (2002).

International Search Report and Written Opinion for PCT/US2007/03431 dated Nov. 19, 2007.

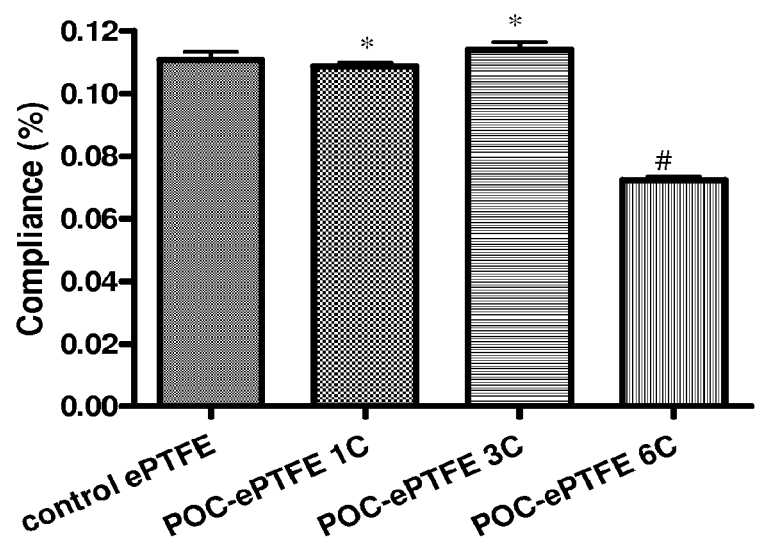
FIGURE 3A-C

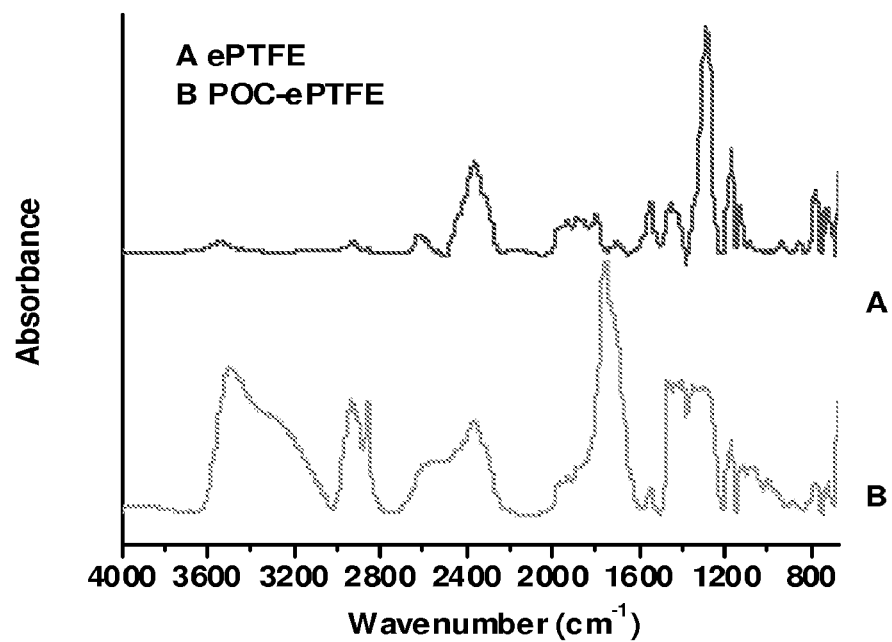
FIGURE 4A-B

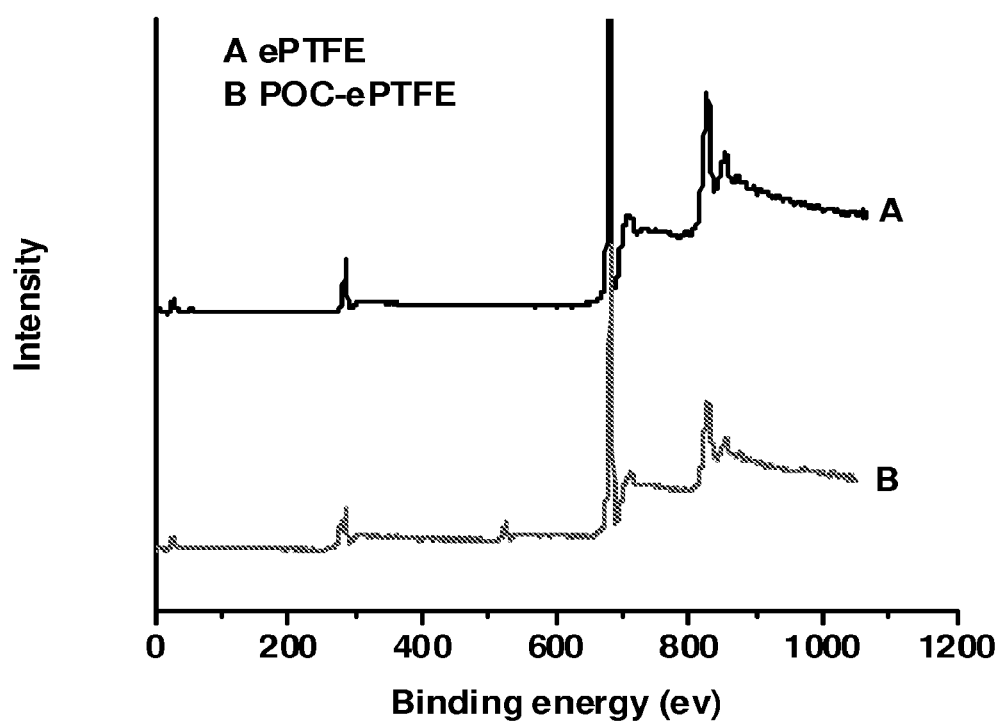
Figure 5A-B

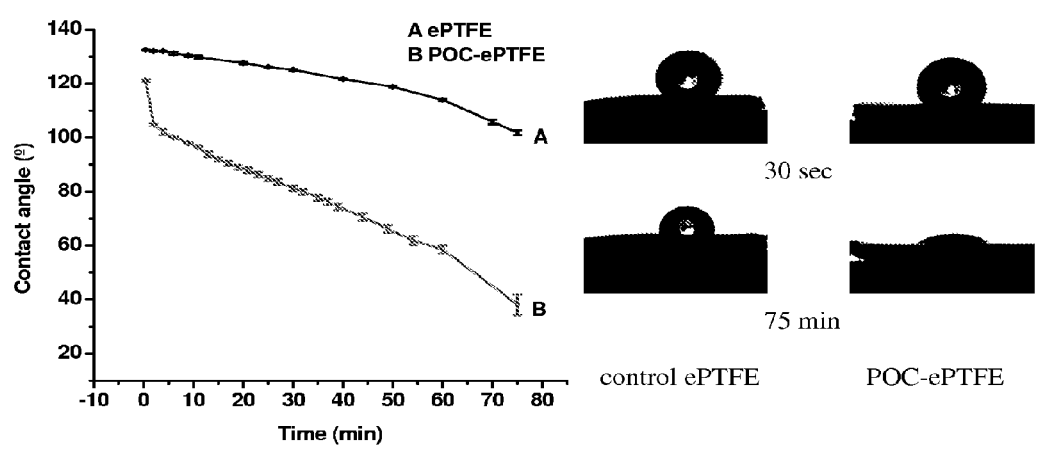
FIGURE 6A-B

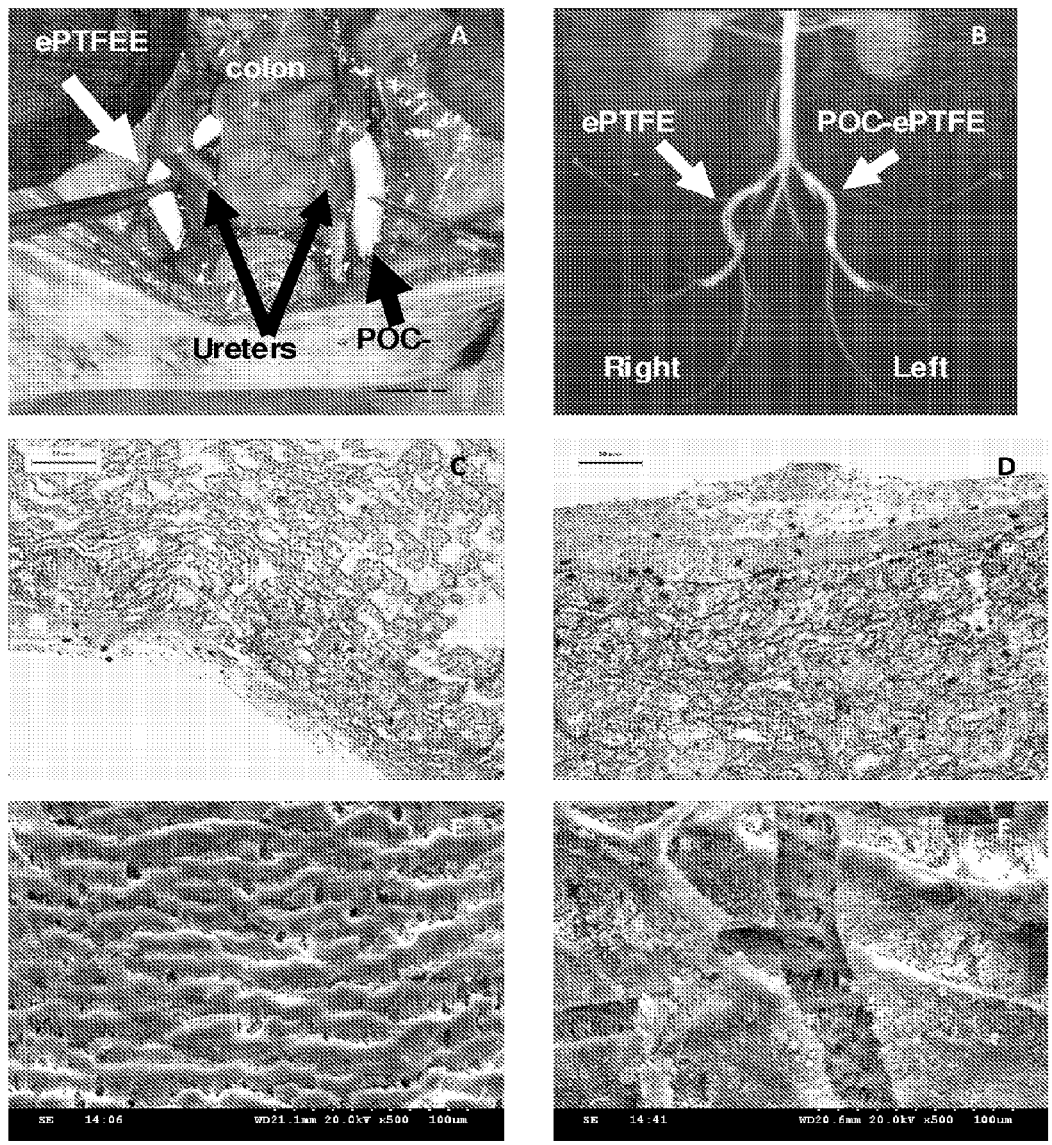
FIGURE 9A-F

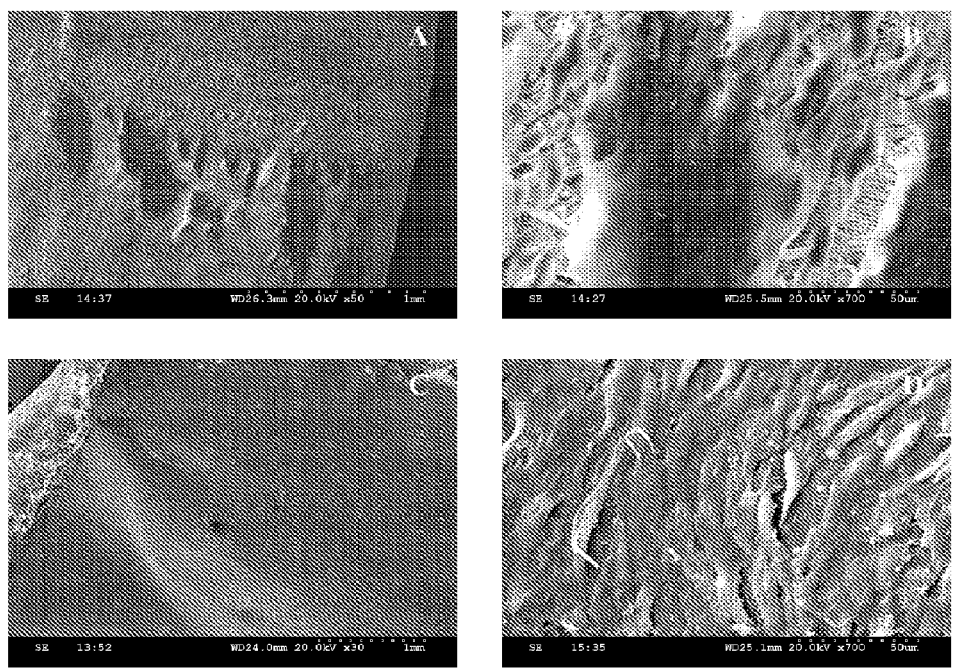
FIGURE 10A-D

FUNCTIONALIZING IMPLANTABLE DEVICES WITH A POLY (DIOL CITRATE) POLYMER The present application claims benefit of U.S. Provisional Application No. 60/771,348 filed Feb. 8, 2006. The entire text of the aforementioned application is incorporated herein by reference

FIELD OF THE INVENTION

The present invention describes methods and compositions for coating implantable devices with a polymer to improve the long-term biocompatibility and/or patency of the device.

BACKGROUND

Implantable medical devices are used in the treatment and assessment of a variety of medical conditions. Such devices may be introduced into the body for a short period of time or may be placed therein permanently and have been used for the treatment of diseased, injured, or deformed body vessels. In cases where malfunctioning body vessels have reduced inner diameters, there is usually reduced flow of vital fluid or gas through the vessels and in extreme cases, the vessels often are occluded. Implantable medical devices have proven useful to open and/or expand, or to otherwise treat such obstructed or constricted vessels. These devices often are placed inside the vessel for a period of time and serve to mechanically support the inside of the malfunctioning vessel to keep the vessel open or patent.

The coated implantable medical device may be partly or completely placed into the esophagus, trachea, colon, biliary tract, urinary tract, vascular system or other location within a human or veterinary patient. Many treatments of the vascular or other systems involve the insertion of a stent, a catheter, a balloon, a wire guide, a cannula or the like into such a location within a human or veterinary patient. A stent is most simply considered as a cylinder of relatively short length which opens a body passage or lumen or which maintains a body passage or lumen in an open condition. In addition, balloons such as angioplasty or dilation balloons are expanded to open a body passage or vessel lumen, thereby causing potential trauma or injury to the expanded passage or vessel.

While implantable medical devices have gained widespread use, they do have attendant drawback. For example, introduction of a stent into the vascular system of a patient may cause the blood vessel walls into which the stent is being placed to become disrupted or injured. Healing of the injury site will involve clot formation (i.e., thrombosis), thereby causing stenosis (i.e., vessel closing) of the blood vessel. Moreover, if the medical device is left within the patient for an extended period of time, thrombus often forms on the device itself, again causing stenosis. As a result, the patient is placed at risk of a variety of complications, including heart attack, pulmonary embolism, and stroke. Thus, the use of such a medical device can entail the risk of precisely the problems that its use was intended to ameliorate.

Another site of injury during implantation of medical devices is the tissue at and beyond the ends of the implanted stent. Regardless of the cause of the trauma or injury to the vessel wall, the tissue will react such as with smooth muscle cell proliferation and the like thereby creating an adverse reaction and subsequent closure or stenosis of the vessel.

Another way in which blood vessels undergo stenosis is through disease. Probably the most common disease causing stenosis of blood vessels is atherosclerosis. Indeed, atherosclerotic vascular disease, in the form of coronary artery and peripheral vascular disease remains the leading cause of mortality in the United States. [1] Many medical devices and therapeutic methods are known for the treatment of atherosclerotic disease. Autogenous veins are the first choice of treatment for vein grafts because of their long-term patency especially in below knee anastomosis. However, for many patients suitable vein grafts are not available. [2] Allografts are in short supply and carry the risk of poor healing characterized by slow wall lysis, compaction and loss of elastic tissue, ulceration, mural thrombosis, and calcification. [3] Large-diameter (>6 mm inner diameter) blood vessels could be replaced by using non-degradable polymeric materials such as Dacron (polyethylene terephthalate) and ePTFE (expanded polytetrafluorotethylene).

Unfortunately, Dacron and ePTFE are not applicable to small-diameter (≤6 mm inner diameter) blood vessels (SDBV), especially in locations below the knee. Synthetic materials trigger inflammatory responses and activate platelets and leukocytes, initiating thrombogenesis and intimal hyperplasia. Poor patency is problematic due in part to incomplete endothelialization, thrombosis, and intimal hyperplasia particularly at the distal anastomosis. [10, 11]

Tissue engineering is an emerging alternative which utilizes biodegradable scaffolds seeded with cells to reconstruct lost tissues or organs. Significant progress has been made for in vitro regeneration of SDBV, [4-6] however, there is still a long way to go before tissue engineered blood vessel substitutes are approved by Food and Drug Adminstration (FDA). [7] Modification of existing vascular grafts to improve performance remains a viable option with room for innovation. It is well known that synthetic grafts do not spontaneously endothelialize in humans. In addition, the highly hydrophobic surfaces of ePTFE grafts limit endothelial cell adhesion. Various modifications have been proposed to either stimulate in vivo graft endothelialization or improve the retention of in vitro seeded endothelial cells when they are exposed to physiological blood flow. [12]. These modifications included coating or immobilization of endothelial-specific adhesion ligands such as collagen, albumin, thrombomodulin, gelatin, fibronectin, collagen-elastin matrices, dipyridamole, fibrin glue, heparin, and peptides (such as RGD, REDV). [13-17] However, issues of stability of the coating, transmission of pathogens, and high costs remain. [18] Plasma treatment is a convenient and widely used method for modifying the surface of materials without altering their bulk properties, [19-23] typically used to confer hydrophilicity to a surface. However, without the inclusion of a polymerizable agent, the plasma-induced effects are temporary and difficult to control. Using plasma to polymerize compounds such as ethylene to form a coating on materials can provide a modified surface that is stable. [24] Nevertheless, the resulting film is normally non-degradable, and long-term biocompatibility and the increased compliance mismatch of the modified grafts are a concern.

It would be desirable to develop implantable medical devices and methods for reliably delivering suitable therapeutic and diagnostic agents, drugs and other bioactive materials directly into a body portion during or following a medical procedure, so as to treat or prevent the abrupt closure and/or restenosis of a body portion such as a passage, lumen or blood vessel.

SUMMARY OF THE INVENTION

The present invention is directed to a novel poly(diol citrates)-based coating for implantable devices. More specifically, the specification describes methods and compositions for making and using implantable devices coated with citric acid copolymers or citric acid copolymers impregnated with therapeutic compositions and/or cells.

More particularly, the present invention provides an implantable medical device wherein at least one surface of said device has deposited thereon a coating comprising a citric acid polyester having the generic formula (A-B-C)n, wherein A is a linear aliphatic dihydroxy monomer; B is citric acid, C is a linear aliphatic dihydroxy monomer, and n is an integer greater than 1.

Preferably, in the citric acid polymer A is a linear diol comprising between about 2 and about 20 carbons. In other embodiments, C is a linear diol comprising between about 2 and about 20 carbons. In some embodiments, both A and C are the same linear diol. In other embodiments A and C are different linear diols. In specific embodiments a preferred linear diol is 1,8-octanediol. In specific embodiments, the linear diol is aliphatic dihydroxy poly 1,8-octanediol co-citric acid. In other embodiments, the linear aliphatic dihydroxy poly 1,10-decanediol co-citric acid.

The base material from which the implantable device is prepared may be any base material that is typically used in medical devices and in prosthetic materials. Exemplary implantable devices may be prepared from one or more materials selected from the group consisting of: stainless steel, tantalum, titanium, nitinol, gold, platinum, inconel, iridium, silver, tungsten, a biocompatible metal, carbon, carbon fiber, cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, a biocompatible polymeric material, polylactic acid, polyglycolic acid, a polyanhydride, polycaprolactone, polyhydroxybutyrate valerate, a biodegradable polymer, a protein, an extracellular matrix component, collagen, fibrin, a biologic agent, PEBAX, polyethylene, irradiated polyethylene or a suitable mixture, copolymer, or alloy of any of these. Preferably, the base material is ePTFE.

In specific preferred embodiments compositions of the present invention are such that they can be used to improve the medical device to give it improved properties for use in blood vessels or any other use for which the base material of the implantable device is used. In particular embodiments, the implantable medical device having the coating of the invention is rendered less thrombogenic than a similar device prepared from ePTFE that lacks said coating.

In preferred embodiments, the coating also may comprise a therapeutic or other agent for delivery to an in vivo site. In specific embodiments, such a therapeutic or other agent may be a bioactive agent wherein the bioactive agent is selected from the group consisting of: an antisense nucleotide, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antimicrobial agent, an antibiotic, an antiplatelet agent, an antimitotic, a microtubule inhibitor, an actin inhibitor, a remodeling inhibitor, an agent for molecular genetic intervention, a cell cycle inhibitor, an inhibitor of the surface glycoprotein receptor, an antimetabolite, an antiproliferative agent, an anti-cancer chemotherapeutic agent, an anti-inflammatory steroid, an immunosuppressive agent, an antibiotic, a radiotherapeutic agent, iodine-containing compounds, barium-containing compounds, a heavy metal functioning as a radiopaque agent, a peptide, a protein, an enzyme, an extracellular matrix component, a cellular component, a biologic agent, an angiotensin converting enzyme (ACE) inhibitor, ascorbic acid, a free radical scavenger, an iron chelator, an antioxidant, a radiolabelled form or other radiolabelled form of any of the foregoing, or a mixture of any of these.

In preferred embodiments, the coating acts as an extracellular matrix to support growth of cells. It may be impregnated with specific factors that facilitate growth of cells, e.g., growth factors, cytokines, chemokines and the like.

In other preferred embodiments, the coating comprises cells selected from the group consisting of endothelial cells, ligament tissue, muscle cells, bone cells, cartilage cells. In preferred embodiments, the coating comprises endothelial cells. In other preferred embodiments, the coating comprises smooth muscle cells. Preferably, the coating will support the growth of cells in vivo such that ultimately those cells are able to form part of the tissue site at which the medical device is implanted.

In other preferred embodiments, the coating further comprises a second polymer selected from the group consisting of poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), and polyester amide.

Also contemplated by the invention is a method of producing engineered tissue, comprising preparing an implantable medical device of the invention as outlined above; and culturing cells of said tissue on the scaffold. The scaffold may be biphasic.

The invention provides methods of decreasing the thrombogenicity of a graft comprising coating said graft with a coating comprising a citric acid polyester having the generic formula (A-B-C)n, wherein A is a linear aliphatic dihydroxy monomer; B is citric acid, C is a linear aliphatic dihydroxy monomer, and n is an integer greater than 1 wherein said graft is less thrombogenic than a similar graft that does not comprise said coating.

In the methods of the invention the coating is preferably deposited on the inner lumen surface of the small diameter blood vessel graft, on the outer surface of the small blood vessel graft or on both the inner lumen surface and the outer surface of the small diameter blood vessel graft. In other preferred embodiments, the graft further comprises a layer of endothelial cells deposited on the surface of said coating. In some preferred methods, the graft further comprises an addition therapeutic agent impregnated into said coating. The therapeutic agent may be selected from the group consisting of an antisense nucleotide, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antimicrobial agent, an antibiotic, an antiplatelet agent, an antimitotic, a microtubule inhibitor, an actin inhibitor, a remodeling inhibitor, an agent for molecular genetic intervention, a cell cycle inhibitor, an inhibitor of the surface glycoprotein receptor, an antimetabolite, an antiproliferative agent, an anti-cancer chemotherapeutic agent, an anti-inflammatory steroid, an immunosuppressive agent, an antibiotic, a radiotherapeutic agent, iodine-containing compounds, barium-containing compounds, a heavy metal functioning as a radiopaque agent, a peptide, a protein, an enzyme, an extracellular matrix component, a cellular component, a biologic agent, an angiotensin converting enzyme (ACE) inhibitor, ascorbic acid, a free radical scavenger, an iron chelator, an antioxidant, a radiolabelled form or other radiolabelled form of any of the foregoing, or a mixture of any of these. In specific embodiments, the therapeutic agent is an anti-inflammatory agent.

In preferred embodiments, the implantable device is one which is formulated for use as small diameter blood vessel and the small diameter blood vessel has an improved property selected from the group consisting of blood flow, vessel tone, platelet activiation, adhesion, and aggregation, leukocyte adhesion, SMC migration and SMC proliferation as compared to a small diameter blood vessel prepared from a graft that does not comprise said coating.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 3 shows the effect of POC coating on the compliance of the ePTFE graft. Compliance of untreated ePTFE grafts (control) and POC-ePTFE grafts with: a) 1 coating, b) 3 coatings and c) 6 coatings. *$P>0.05$ vs. control; #$P<0.05$ vs. control.

FIG. 4 shows the surface FTIR analysis of coated and uncoated grafts. A) untreated ePTFE and B) ePTFE with 3 coatings of POC.

FIG. 5 shows XPS analysis of the grafts. A) control; and B) POC-ePTFE with 3 coatings.

FIG. 6 shows the effect of POC coating on water-in-air contact angle. A) untreated ePTFE; and B) POC-ePTFE graft with 3 coatings.

FIG. 9 shows In vivo assessment in pigs of the foreign body reaction to the grafts. A) Intraoperative photo of the implanted grafts. (B) contrast-enhanced MR angiogram demonstrating patency of both grafts at 7 days, 1=ligated native common iliac arteries. C) MAC 387 stain for new macrophages and granulocyte (arrowheads) on POC-ePTFE graft; D) MAC 387 stain for new macrophages and granulocyte (arrowheads) on control ePTFE graft; L=lumen of the graft. Scale bars=50 μm E) and (F): SEM of the lumen of the grafts. Scale bars=100 μm.

FIG. 10 shows representative SEM photographs of endothelial progenitor cells (EPCs) that were cultured on ePTFE graft (A and B) and POC-ePTFE graft (C and D) for 10 days. Scale bar: A and C 1 mm; B and D 50 μm.

DESCRIPTION OF THE PREFERRED EMBODIMENTS

Figure 1:
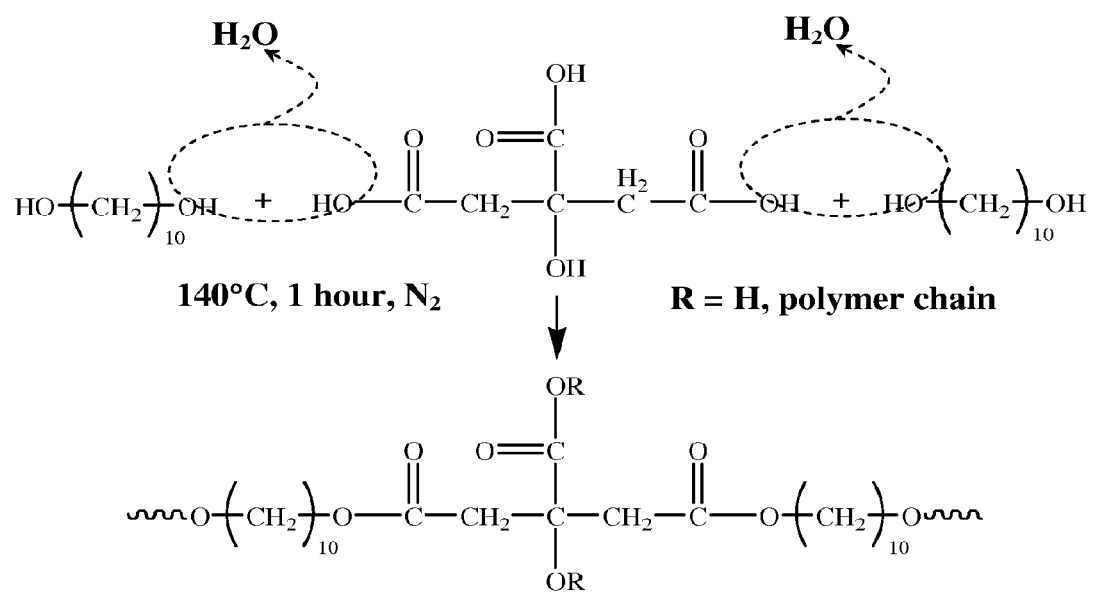
FIG. 1 is a schematic representation of the synthesis of poly(1,8-octanediol-co-citric acid).

While there are numerous technologies available for the treatment and prevention of disorders resulting from occluded or damaged vessels that are based on the use of implantable medical devices, there is a need for improved implantable devices. It would be desirable to produce such implantable devices that have improved biocompatibility, cell adhesion properties, endothelialization as well as to decrease thrombogenicity. Further, it would be desirable to limit the systemic exposure of a subject to the bioactive materials that are being used in the treatment regimen, particularly when the agent is a toxic, or chemotherapeutic agent being delivered to a specific site of action through an intravenous catheter (which itself has the advantage of reducing the amount of agent needed for successful treatment), by preventing stenosis both along the catheter and at the catheter tip. It would be desirable to similarly improve other therapies. Of course, it would also be desirable to avoid degradation of the agent, drug or bioactive material during its incorporation on or into any such device. It would further be highly desirable to develop a method for coating an implantable medical device with a drug, therapeutic agent, diagnostic agent or other bioactive material which entailed a minimum number of steps, thereby reducing the ultimate cost of treating the patient. It would be desirable to deliver the bioactive material without causing additional problems with a poor biocompatible carrier or containment material. Finally, it would be highly desirable to develop a method for coating an implantable medical device with a drug, therapeutic agent, diagnostic agent or other bioactive material which could be carried out in such a way as to minimize any environmental or personal risks or inconveniences associated with the manufacture of the device.

Tissue engineering is an emerging alternative which utilizes biodegradable scaffolds seeded with cells to reconstruct lost tissues or organs. Significant progress has been made for in vitro regeneration of small diameter blood vessels (SDBV), [4-6] however, there is still a long way to go before tissue engineered blood vessel substitutes are approved by Food and Drug Administration (FDA). [7] Modification of existing vascular grafts to improve performance remains a viable option with room for innovation. The intrinsic hydrophobicity of ePTFE grafts limit the ability of endothelial cell to adhere to them.

By way of explanation, a functional endothelium provides a continuous thromboresistant layer between blood and the blood vessel wall. It also controls blood flow and vessel tone, platelet activation, adhesion and aggregation, leukocyte adhesion, and SMC migration and proliferation. [25] Mammalian cells maintained in vitro require nutrients and growth factors but also require an appropriate substratum upon which to attach and spread. The intrinsic hydrophobicity of ePTFE grafts limit the ability of endothelial cell to adhere to them. Previous studies have confirmed that ECs are able to secrete extracellular matrix (ECM). [8,9] To date, no vascular graft has successfully achieved long-term patency when used for SDBV applications. The synthetic graft market is currently dominated by ePTFE and Dacron; therefore, we are proposing a novel approach which could significantly reduce the thrombogenicity of ePTFE grafts, thereby facilitating their use in SDBV applications. As of yet, no one has investigated the use of a synthetic biodegradable scaffold as a means to create a more stable and functional endothelial cell monolayer on ePTFE grafts.

The present invention describes implantable medical devices suitable for use inside or outside anatomical structures, such as body vessels (e.g., vessels of the vasculature like blood vessels). The invention is based the principle of coating ePTFE grafts using our own newly developed coating technique, a spin-shearing method, with biodegradable elastomeric polymers are used as coating materials, which could be any other biodegradable elastomers currently available in the market, such as poly(diol citrates) and its derivatives, polyurethane and its derivatives, polycarbonate and its derivatives, polyhydroxyalkanoates (PHAs) and their derivatives, or aliphatic biodegradable polyester elastomers (such as poly(glycolide-co-caprolactone)(PGCL), polycaprolactone (PCL), poly(glycerol sebacate)(PGS)). Particularly preferred materials are poly(diol citrates) and their derivatives. The biodegradable elastomeric polymers could be mixed with other materials to modify the grafts. The coating can be applied on either the lumen or outside or both inside and outside of grafts.

In exemplary embodiments, the spin-shearing method is performed to prepare a small diameter blood vessel or similar graft from ePTFE, comprising modifying the lumen of said small diameter blood vessel by coating the small diameter blood vessel through a spin-shearing method wherein said method comprises coating a glass-rod with said citric acid polymer by use of a mechanical stirrer; rotating said coated glass rod at a low speed of about 300 rpm; contacting said rotating glass rod with ePTFE or other materials used to form the coating; shearing the lumen of the graft by rotating the graft in a direction counter to the direction in which it is spinning. These steps optionally are repeated 2, 3, 4, 5, 6, 7, 8 or more times.

The grafts can contain endothelial cells, stem cells, or endothelial progenitor cells (EPCs) which can be grown on the graft to form an endothelium layer on top of the underlying polymer coating. In addition, or as an alternative, the coating may be impregnated with a therapeutic agent such as any anticoagulant and anti-inflammation drugs or any other therapeutic agent that it is desired to release at the site at which the device is implanted. In certain embodiments, NO-release agents could be incorporated into the polymer coating for controlled release.

The present invention for the first time shows the use of a novel biodegradable elastomeric polymer, poly(diol citrates) to modify the ePTFE graft via a convenient method to tissue engineer an endothelium. A particularly preferred method to accomplish this is the spin-shearing method. In preferred embodiments, the vascular graft was coated with a POC elastic polymer on the graft lumen via an interfacial in-situ polycondensation method. This layer of biodegradable elastic coating is expected to support attachment, proliferation and gene expression of the endothelial cells (ECs) without significantly altering the mechanical properties of the vessel. This is done by facilitating mechanical interlocking between secreted extracellular matrix and ePTFE fibrils in the lumen of the graft. As the polymer degrades, it will be replaced by an endothelium and its secreted extracellular matrix, improving EC retention under dynamic flow conditions. In addition, this approach also allows controlled delivery of anti-inflammatory drugs or other nitric oxide (NO) releasing compounds by incorporating them in the post-polymerization reaction resulting in a drug-loaded graft. The resultant vascular graft could serve better for coronary and peripheral vascular replacement, and potentially as a viable option in small-diameter blood vessel applications. This method to modify the vascular graft can be extended to other medical implants and devices such as devices prepared for implantation to replace valves, bones and other prosthetic structures. It is contemplated that the coatings prepared according to the present invention will improve the biocompatibility and comfort of use of such devices. Such devices may be prepared from a base material that comprises one or more materials selected from the group consisting of: stainless steel, tantalum, titanium, nitinol, gold, platinum, inconel, iridium, silver, tungsten, a biocompatible metal, carbon, carbon fiber, cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, a biocompatible polymeric material, polylactic acid, polyglycolic acid, a polyanhydride, polycaprolactone, polyhydroxybutyrate valerate, a biodegradable polymer, a protein, an extracellular matrix component, collagen, small intestine submucosa (SIS), fibrin, a biologic agent, PEBAX, polyethylene, irradiated polyethylene or a suitable mixture, copolymer, or alloy of any of these.

Compositions of poly(diol citrates) that are used to coat the implantable medical device comprise a citric acid polyester having the generic formula (A-B-C)n, wherein A and C could be any of the diols or any combination of the diols; B could be citric acid, malic acid or their combinations. The diols include linear or non-linear aliphatic diols, branched diol, cyclodiol, triol, heteroatom containing diol (such as N-methyldiethanolamine, MDEA) and macrodiol or their combinations. Any medical device coated with any biodegradable elastomers (e.g. poly diol-citric acid, polyurethanes, polycaprolactone and copolymers thereof) is contemplated to be within the aspects of the present invention.

POC has been shown to be compatible (i.e. as per cell adhesion, proliferation, and differentiation assays) with several cell types including human and pig endothelial cells, human and pig smooth muscle cells, bovine chondrocytes, and bovine fibroblasts [16, 30]. It was also shown to be biocompatible in vivo in a rat subcutaneous implantation model [15]. In another co-pending application, the favorable cell adhesion and spreading characteristics of POC were confirmed in vitro with the use of primary human osteoblasts.

Poly(diol citrates) are a family of biodegradable and biocompatible elastomers that have shown significant potential for soft tissue engineering, see e.g., U.S. patent application 60/721,687 and applications depending therefrom. However, while those prior compositions are useful in the production of matrices for tissue culture and implantable tissue patches, those compositions have not previously been demonstrated for coating implantable devices to produce devices that will be useful in implantable devices and in coating prostheses and other implantable devices. The methods and compositions of the present invention are directed to the use of poly(diol citrate) based polymers to prepare improved implantable devices.

Methods and compositions for preparing POC are described in detail in PCT/US2004/030631 and U.S. 60/721,687, each of which is incorporated herein by reference in its entirety. Briefly, equimolar amounts of citric acid and 1,8-octanediol were stirred and melted together at 160° C. for 15 minutes, decrease temperature to 140° C. and continue stirring for 1 hr. The pre-polymer is purified by precipitation in water and then post-polymerized at 80° C. for 2 days. The pre-polymer is soluble in ethanol or 1,4-dioxane, which are less toxic than other commonly used solvents. The mechanical properties and degradation rates of the elastomer can be modulated by controlling synthesis conditions such as crosslinking temperature and time, vacuum, choice of diol, and initial monomer molar ratio. [28] No permanent deformation was found during mechanical tests. Other poly(diol citrates) could also be synthesized using the method described above. Polycondensation of poly(diol citrates) can be conducted under no vacuum, no catalyst, and low reaction temperature (under 100° C., such as 60° C., 80° C., even as low as 37° C.). Catalyst and high temperature could also be applied if needed.

Composition of poly(diol citrates) comprise a citric acid polyester having the generic formula (A-B-C)n, wherein A and C could be any of the diols or any combination of the diols; B could be citric acid, malic acid or their combinations. The diols include aliphalic diols or branched diols, cyclodiols, triols, heteroatom-containing diols and macrodiols or their combinations;

In addition to the POC-based polymers, it is contemplated that the implantable devices may further be coated with another biodegradable and biocompatible polymer. Two such polymers are poly(L-lactic acid) (PLLA) and poly(lactic-co-glycolic acid) (PLGA). These polymers are rigid and strong and have been used in many tissue engineering applications. Furthermore, the rate of degradation could be tailored to match that of the surrounding elastomeric matrix. Poly(L-lactic acid) has a degradation time of greater than two years while poly(glycolic acid) has a degradation time of 1-2 months. By changing the ratio of lactic to glycolic acid, the degradation rate could be varied from fast (1-2 months) to slow (>2 years). For tissue engineering, the rate of degradation of the polymer scaffold should match that of tissue regrowth.

The polymer may be a biodegradable polymer or a non-biodegradable polymer, but preferably is a biodegradable polymer. Biodegradable polymers include, but are not limited to collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly (caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of .epsilon.-caprolactone and lactide, copolymers of glycolide and .epsilon.-caprolactone, copolymers of lactide and 1,4-dioxane-2-one, polymers and copolymers that include one or more of the residue units of the monomers D-lactide, L-lactide, D,L-lactide, glycolide, .epsilon.-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly (ethylene terephthalate), poly(malic acid), poly(tartronic acid), polyanhydrides, polyphosphazenes, poly(amino acids). The biodegradable polymers used herein may be copolymers of the above polymers as well as blends and combinations of the above polymers. (see generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

In particular preferred embodiments, the biodegradable or resorbable polymer is one that is formed from one or more monomers selected from the group consisting of lactide, glycolide, ε-caprolactone, trimethylene carbonate, 1,4-dioxan-2-one, 1,5-dioxepan-2-one, 1,4-dioxepan-2-one, hydroxyvalerate, and hydroxybutyrate. In one aspect, the polymer may include, for example, a copolymer of a lactide and a glycolide. In another aspect, the polymer includes a poly (caprolactone). In yet another aspect, the polymer includes a poly(lactic acid), poly(L-lactide)/poly(D,-L-Lactide) blends or copolymers of L-lactide and D,L-lactide. In yet another aspect, the polymer includes a copolymer of lactide and ε-caprolactone. In yet another aspect, the polymer includes a polyester (e.g., a poly(lactide-co-glycolide). The poly(lactide-co-glycolide) may have a lactide:glycolide ratio ranges from about 20:80 to about 2:98, a lactide:glycolide ratio of about 10:90, or a lactide:glycolide ratio of about 5:95. In one aspect, the poly(lactide-co-glycolide) is poly(L-lactide-co-glycolide; see e.g., U.S. Pat. No. 6,531,146 and U.S. application No. 2004/0137033.). Other examples of biodegradable materials include polyglactin, and polyglycolic acid.

Representative examples of non-biodegradable compositions include ethylene-co-vinyl acetate copolymers, acrylic-based and methacrylic-based polymers (e.g., poly(acrylic acid), poly(methylacrylic acid), poly(methylmethacrylate), poly(hydroxyethyl methacrylate), poly(alkylcynoacrylate), poly(alkyl acrylates), poly(alkyl methacrylates)), polyolefins such as poly(ethylene) or poly(propylene), polyamides (e.g., nylon 6,6), poly(urethanes) (e.g., poly(ester urethanes), poly (ether urethanes), poly(carbonate urethanes), poly(esterurea)), polyesters (e.g., PET, polybutyleneterephthalate, and polyhexyleneterephthalate), olyethers (poly(ethylene oxide), poly(propylene oxide), poly(ethylene oxide)-poly(propylene oxide) copolymers, diblock and triblock copolymers, poly (tetramethylene glycol)), silicone containing polymers and vinyl-based polymers (polyvinylpyrrolidone, poly(vinyl alcohol), poly(vinyl acetate phthalate), poly(styrene-co-isobutylene-co-styrene), fluorine containing polymers (fluoropolymers) such as fluorinated ethylene propylene (FEP) or polytetrafluoroethylene (e.g., expanded PTFE).

The polymers may be combinations of biodegradable and non-biodegradable polymers. Further examples of polymers that may be used are either anionic (e.g., alginate, carrageenin, hyaluronic acid, dextran sulfate, chondroitin sulfate, carboxymethyl dextran, caboxymethyl cellulose and poly (acrylic acid)), or cationic (e.g., chitosan, poly-I-lysine, polyethylenimine, and poly(allyl amine)) (see generally, Dunn et al., J. Applied Polymer Sci. 50:353, 1993; Cascone et al., J. Materials Sci.: Materials in Medicine 5:770, 1994; Shiraishi et al., Biol. Pharm. Bull. 16:1164, 1993; Thacharodi and Rao, Int'l J. Pharm. 120:115, 1995; Miyazaki et al., Int'l J. Pharm. 118:257, 1995). Preferred polymers (including copolymers and blends of these polymers) include poly(ethylene-co-vinyl acetate), poly(carbonate urethanes), poly(hydroxyl acids) (e.g., poly(D,L-lactic acid) oligomers and polymers, poly(L-lactic acid) oligomers and polymers, poly(D-lactic acid) oligomers and polymers, poly(glycolic acid), copolymers of lactic acid and glycolic acid, copolymers of lactide and glycolide, poly(caprolactone), copolymers of lactide or glycolide and ε-caprolactone), poly(valerolactone), poly(anhydrides), copolymers prepared from caprolactone and/or lactide and/or glycolide and/or polyethylene glycol.

Methods for making POC-PLLA or PLGA or other like composites are described in U.S. 60/721,687.

In specific embodiments, the compositions of the invention (i.e., the compositions that are made up of a poly(diol citrate) polymer) are used to coat the inner lumen of an implantable device. Such a coating may be comprised of just the poly(diol citrate) or the polymer may be impregnated or otherwise loaded with a drug or other biologically active agent to be delivered (e.g., in a controlled-release manner) or it may be seeded with cells so that they can act as cellular tissue patches or tissue grafts.

In specific embodiments, the POC materials made according to the methods of the present invention will be useful both as substrata for the growth and propagation of tissues cells that may be seeded on the substrata and also as coating on the implantable devices. In those embodiments where the elastomeric composites are used in bioimplantable devices, the substrate may be formulated into a shape suitable for implantation. For example, as described in U.S. Pat. No. 6,620,203 (incorporated herein by reference), it may be desirable to produce prosthetic organ tissue for implantation into an animal, such as e.g., testicular tissue described in the U.S. Pat. No. 6,620,203. Other organs for which tissue implantation patches may be generated include, but are not limited to skin tissue for skin grafts, myocardial tissue, bone tissue for bone regeneration, testicular tissue, endothelial cells, blood vessels, and any other cells from which a tissue patch may be generated. Thus, those of skill in the art would understand that the aforementioned organs/cells are merely exemplary organs/cell types and it should be understood that cells from any organ may be seeded onto the biocompatible elastomeric composites of the invention to produce useful tissue for implantation and/or study.

The cells that may be seeded onto the POC or other polymers of the present invention may be derived from commercially available cell lines, or alternatively may be primary cells, which can be isolated from a given tissue by disaggregating an appropriate organ or tissue which is to serve as the source of the cells being grown. This may be readily accomplished using techniques known to those skilled in the art. Such techniques include disaggregation through the use of mechanically forces either alone or in combination with digestive enzymes and/or chelating agents that weaken cell-cell connections between neighboring cells to make it possible to disperse the tissue into a suspension of individual cells without appreciable cell breakage. Enzymatic dissociation can be accomplished by mincing the tissue and treating the minced tissue with any of a number of digestive enzymes either alone or in combination. Digestive enzymes include but are not limited to trypsin, chymotrypsin, collagenase, elastase, and/or hyaluronidase, Dnase, pronase, etc. Mechanical disruption can also be accomplished by a number of methods including, but not limited to the use of grinders, blenders, sieves, homogenizers, pressure cells, or sonicators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the primary cells are disaggregated, the cells are separated into individual cell types using techniques known to those of skill in the art. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168. Media and buffer conditions for growth of the cells will depend on the type of cell and such conditions are known to those of skill in the art.

In certain embodiments, it is contemplated that the cells attached to the biocompatible elastomeric composite substrates of the invention are grown in bioreactors. A bioreactor may be of any class, size or have any one or number of desired features, depending on the product to be achieved. Different types of bioreactors include tank bioreactors, immobilized cell bioreactors, hollow fiber and membrane bioreactors as well as digesters. There are three classes of immobilized bioreactors, which allow cells to be grown: membrane bioreactors, filter or mesh bioreactors, and carrier particle systems. Membrane bioreactors grow the cells on or behind a permeable membrane, allowing the nutrients to leave the cell, while preventing the cells from escaping. Filter or mesh bioreactors grow the cells on an open mesh of an inert material, allowing the culture medium to flow past, while preventing the cells from escaping. Carrier particle systems grow the cells on something very small, such as small nylon or gelatin beads. The bioreactor can be a fluidized bed or a solid bed. Other types of bioreactors include pond reactors and tower fermentors. Any of these bioreactors may be used in the present application for regenerating/engineering tissues on the citric acid based elastomeric compositions of the present invention.

Certain tissues that are regenerated by use of the citric acid based elastomeric composition of the invention may be encapsulated so as to allow the release of desired biological materials produced by the cells at the site of implantation, while sequestering the implanted cells from the surrounding site. Cell encapsulation can be applied to all cell types secreting a bioactive substance either naturally or through genetic engineering means. In practice, the main work has been performed with insulin secreting tissue.

Encapsulation procedures are most commonly distinguished by their geometrical appearance, i.e. micro- or macro-capsules. Typically, in microencapsulation, the cells are sequestered in a small permselective spherical container, whereas in macroencapsulation the cells are entrapped in a larger non-spherical membrane, Lim et al. (U.S. Pat. Nos. 4,409,331 and 4,352,883) discloses the use of microencapsulation methods to produce biological materials generated by cells in vitro, wherein the capsules have varying permeabilities depending upon the biological materials of interest being produced, Wu et al, Int. J. Pancreatology, 3:91-100 (1988), disclose the transplantation of insulin-producing, microencapsulated pancreatic islets into diabetic rats.

As indicated above, the cells that are seeded on the elastomeric composites of the present invention may be cell lines or primary cells. In certain preferred embodiments, the cells are genetically engineered cells that have been modified to express a biologically active or therapeutically effective protein product. Techniques for modifying cells to produce the recombinant expression of such protein products are well known to those of skill in the art. In particular preferred embodiments, the compositions of the invention may be used to form of a tissue graft or tissue patch. Endothelial cells are particularly preferred. Smooth muscle cells also may be used. The cells for the tissue graft may be an autograft, allograft, biograft, biogenic graft or xenograft.

Tissue grafts may be derived from various tissue types. Representative examples of tissues that may be used to prepare biografts include, but are not limited to, rectus sheaths, peritoneum, bladder, pericardium, veins, arteries, diaphragm and pleura. For such grafts the cells may be endothelial cells, ligament tissue, muscle cells, bone cells, cartilage cells. Such cells may be grafted into the compositions of the invention alone or in combination with a drug or biologically active agent to be delivered to an in vivo site. For example, such cells for the biograft may be harvested from a host, loaded with the agent of interest and then applied in a perivascular manner at the site where lesions and intimal hyperplasia can develop. Once implanted, the agent of interest (e.g., paclitaxel and/or rapamycin) is (are) released from the graft and can penetrate the vessel wall to prevent the formation of intimal hyperplasia at the treatment site. In certain embodiments, the biograft may be used as a backing layer to enclose a composition (e.g., a gel or paste loaded with anti-scarring agent).

The patches made of the compositions of the present invention may be combined with drugs for delivery or therapeutic agents that can form part of a tissue patch prepared from the polymers of the invention. For example, the compositions of the invention may be used to form a mesh or a patch made of the biodegradable polymeric matrix that conforms to the tissue and releases the agent (e.g., a therapeutic agent such as a drug or a diagnostic agent such as a marker, dye or other marker of that will allow visualization of a diseased state). In preferred examples, the compositions are fashioned into coating on the surface (inner, outer or inner and outer surface of an implantable device such as an ePTFE-based device for use in angioplasty). Such a coating also may incorporate a drug that can be released in a controlled release manner. See, e.g., U.S. Pat. No. 6,461,640. Such a drug may be present in the coating alone, or alternatively, the coating also may comprise cells that form e.g., an endothelial layer that coats a surface of the implantable device. The drug may be any therapeutic agent.

The coating made of the compositions of the invention may be impregnated with an antioxidant and/or antimicrobial. See, e.g., U.S. Pat. No. 6,572,878. The tissue patch made of the cells, the ePTFE compound and the coating of the compositions of the invention may be prepared to be wrapped around a nerve in a canal to reduce fibroplasia. See, e.g., U.S. Pat. No. 6,106,558. The tissue patch may be a resorbable collagen membrane that is wrapped around the spinal chord to inhibit cell adhesions. See, e.g., U.S. Pat. No. 6,221,109. The tissue patch may be used as a dressing to cover a wound and promote wound healing. See, e.g., U.S. Pat. No. 6,548,728. The compositions of the present invention may be prepared as a bandage that contains a scar treatment pad with a layer of silicone elastomer or silicone gel. See, e.g., U.S. Pat. Nos. 6,284,941 and 5,891,076. The compositions may be used to incorporate a biologically active compound. See, e.g., U.S. Pat. Nos. 6,323,278; 6,166,130; 6,051,648 and 5,874,500.

Methods for incorporating the biologically active material onto or into the coating of the present invention include: (a) affixing (directly or indirectly) to the patch such a biologically active material (e.g., by either a spraying process or dipping process as described above, with or without a carrier), (b) incorporating or impregnating a biologically active material into the coating made with the composition (e.g., by either a spraying process or dipping process as described above, with or without a carrier), (c) by coating the coating made with the composition with a substance such as a hydrogel which will in turn absorb the biologically active material, (d) constructing the patch made with the composition itself with the biologically active material in either the biodegradable polymer, the poly(diol citrate) polymer, or in the mixture of the two, or (e) by covalently binding the biologically active material directly to the surface of the composition of the invention.

In specific and preferred embodiments, the poly(diol citrate) compositions of the present invention are used to coat devices such as medical stents and the like. For devices that are coated, the coating process can be performed in such a manner as to (a) coat only one surface of device with the compositions of the invention or (b) coating all or parts of the device with the compositions of the invention.

The poly(diol citrate)-based coatings or devices coated with the same may be made sterile either by preparing them under aseptic environment and/or they may be terminally sterilized using methods known in the art, such as gamma radiation or electron beam sterilization methods or a combination of both of these methods.

Thus, the therapeutic agent may advantageously be delivered to adjacent tissues or tissues proximal to the implant site. Biologically-active agents which may be used alone or in combination in the implant precursor and implant include, for example, a medicament, drug, or other suitable biologically-, physiologically-, or pharmaceutically-active substance which is capable of providing local or systemic biblogical, physiological, or therapeutic effect in the body of the patient. The biologically-active agent is capable of being released from the solid implanted matrix into adjacent or surrounding tissue fluids during biodegradation, bioerosion, or bioresorption of the implant made from the compositions of the invention.

Other agents also may be used in the coating compositions of the invention. Preferably, such agents are capable of preventing infection in the host, either systemically or locally at the defect site, are contemplated as illustrative useful additives. These additives include anti-inflammatory agents, such as hydrocortisone, prednisone, and the like, NSAIDS, such as acetaminophen, salicylic acid, ibuprofen, and the like, selective COX-2 enzyme inhibitors, antibacterial agents, such as penicillin, erythromycin, polymyxin B, viomycin, chloromycetin, streptomycins, cefazolin, ampicillin, azactam, tobramycin, cephalosporins, bacitracin, tetracycline, doxycycline, gentamycin, quinolines, neomycin, clindamycin, kanamycin, metronidazole, and the like, antiparasitic agents such as quinacrine, chloroquine, vidarabine, and the like, antifungal agents such as nystatin, and the like, antiviricides, particularly those effective against HIV and hepatitis, and antiviral agents such as acyclovir, ribarivin, interferons, and the like. Systemic analgesic agents such as salicylic acid, acetaminophen, ibuprofen, naproxen, piroxicam, flurbiprofen, morphine, and the like, and local anaesthetics such as cocaine, lidocaine, bupivacaine, xylocaine, benzocaine, and the like, also can be used as additives in the composites.

Other therapeutic agents include bioactive agents such as those selected from the group consisting of: an antisense nucleotide, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antimicrobial agent, an antibiotic, an antiplatelet agent, an antimitotic, a microtubule inhibitor, an actin inhibitor, a remodeling inhibitor, an agent for molecular genetic intervention, a cell cycle inhibitor, an inhibitor of the surface glycoprotein receptor, an antimetabolite, an antiproliferative agent, an anti-cancer chemotherapeutic agent, an anti-inflammatory steroid, an immunosuppressive agent, an antibiotic, a radiotherapeutic agent, iodine-containing compounds, barium-containing compounds, a heavy metal functioning as a radiopaque agent, a peptide, a protein, an enzyme, an extracellular matrix component, a cellular component, a biologic agent, an angiotensin converting enzyme (ACE) inhibitor, ascorbic acid, a free radical scavenger, an iron chelator, an antioxidant, a radiolabelled form or other radiolabelled form of any of the foregoing, or a mixture of any of these.

In yet another aspect, the implantable device coatings made from the compositions of the invention may be used for delivering a specific therapeutic or other agent to an external portion (surface) of a body passageway or cavity. Examples of body passageways include arteries, veins, the heart, the esophagus, the stomach, the duodenum, the small intestine, the large intestine, biliary tracts, the ureter, the bladder, the urethra, lacrimal ducts, the trachea, bronchi, bronchiole, nasal airways, Eustachian tubes, the external auditory mayal, vas deferens and fallopian tubes. Examples of cavities include the abdominal cavity, the buccal cavity, the peritoneal cavity, the pericardial cavity, the pelvic cavity, perivisceral cavity, pleural cavity and uterine cavity.

Example 1

Biodegradable Elastomeric Polymers

The coating compositions of the invention are based on biodegradable elastomeric polymers of poly(diol) citrate molecules. Such molecules typically comprising a polyester network of citric acid copolymerized with a linear aliphatic di-OH monomer in which the number of carbon atoms ranges from 2 to 20. Polymer synthesis conditions for the preparation of these molecules vary from mild conditions, even at low temperature (less than 100° C.) and no vacuum, to tough conditions (high temperature and high vacuum) according the requirements for the materials properties. By changing the synthesis conditions (including, but not limited to, post-polymerization temperature, time, vacuum, the initial monomer molar ratio, and the di-OH monomer chain length) the mechanical properties of the polymer can be modulated over a wide range. This series of polymers exhibit a soft, tough, biodegradable, hydrophilic properties and excellent biocompatibility in vitro.

The poly(diol)citrate polymers used herein have a general structure of:

(A-B-C)$_n$

Where A is a linear, aliphatic diol and C also is a linear aliphatic diol. B is citric acid. The citric acid co-polymers of the present invention are made up of multiples of the above formula, as defined by the integer n, which may be any integer greater than 1. It is contemplated that n may range from 1 to about 1000 or more. It is particularly contemplated that n may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 31, 32, 33, 34, 35, 36, 37, 38, 39, 40, 41, 42, 43, 44, 45, 46, 47, 48, 49, 50, or more.

In preferred embodiments, the identity of "A" above is poly 1,10-decanediol and in another preferred embodiment the identity of A is 1,8-octanediol. However, it should be understood that these are merely exemplary linear, aliphatic diols. Those of skill are aware of other aliphatic alcohols that will be useful in polycondensation reactions to produce citric acid polymers. Exemplary such aliphatic diols include any diols of between about 2 carbons and about 20 carbons. While the diols are preferably aliphatic, linear, unsaturated diols, with the hydroxyl moiety being present at the $C_1$ and $C_x$ position (where x is the terminal carbon of the diol), it is contemplated that the diol may be an unsaturated diol in which the aliphatic chain contains one or more double bonds. The preferred identity for "C" in one embodiment is 1,8-octanediol, however as with moiety "A," "C" may be any other aliphatic alcohols. While in specific embodiments, both A and C are both the same diol, e.g., 1,8-octanediol, it should be understood that A and C may have different carbon lengths. For example, A may be 2, 3, 4, 5, 6, 7, 8, 9, 10, 11, 12, 13, 14, 15, 16, 17, 18, 19, 20 or more carbons in length, and C may independently be 2, 3, 4, 5, 6, 7, 8, 9, 10, 11, 12, 13, 14, 15, 16, 17, 18, 19, 20 or more carbons in length. Exemplary methods for the polycondensation of the citric acid with the linear diols are provided in this Example. These materials are then used as starting materials for the grafts described in Example 2.

Synthesis of Poly(1,10-decanediol-co-citric acid) (PDC)

In a typical experiment, 19.212 g citric acid and 17.428 g 1,10-decanediol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly(1,10-decanediol-co-citric acid). Nitrogen was introduced into the reaction system before the polymer was taken out from reaction system.

Preparation of Poly(1,8-Octanediol-co-citric acid) (POC)

In a typical experiment, 19.212 g citric acid and 14.623 g octanediol were added to a 250 mL three-neck round-bottom flask, fitted with an inlet adapter and an outlet adapter. The mixture was melted within 15 min by stirring at 160-165° C. in silicon oil bath, and then the temperature of the system was lowered to 140° C. The mixture was stirred for another 1 hr at 140° C. to get the pre-polymer. Nitrogen was vented throughout the above procedures. The pre-polymer was post-polymerized at 60° C., 80° C. or 120° C. with and without vacuum for predetermined time (from one day to 3 weeks depending on the temperature, with the lower temperatures requiring longer times) to achieve the Poly(1,8-octanediol-co-citric acid). Nitrogen was introduced into the reaction system before the polymer was taken out from the reaction system.

Porous scaffolds of POC (tubular and flat sheets) were prepared via a salt leaching technique as follows: POC pre-polymer was dissolved into dioxane to form a 25 wt % solution, and then the sieved salt (90-120 microns) was added into pre-polymer solution to serve as a porogen. The resulting slurry was cast into a poly(tetrafluoroethylene) (PTFE) mold (square and tubular shape). After solvent evaporation for 72 h, the mold was transferred into a vacuum oven for post-polymerization. The salt in the resulting composite was leached out by successive incubations in water (produced by Milli-Q water purification system every 12 h for a total 96 h. The resulting porous scaffold was air-dried for 24 hr and then vacuum dried for another 24 hrs. The resulting scaffold was stored in a dessicator under vacuum before use. Porous scaffolds are typically preferred when cells are expected to migrate through a 3-dimensional space in order to create a tissue slice. Solid films would be used when a homogenous surface or substrate for cell growth is required such as an endothelial cell monolayer within the lumen of a vascular graft.

Using similar techniques, porous scaffolds of PDC or other poly(diol)citrates can be prepared. In other embodiments, biphasic scaffolds can be prepared. Biphasic scaffolds consist of an outside porous phase and an inside non-porous phase as depicted in the schematic drawing shown in FIG. 15 of PCT PCT/US2004/030631, incorporated herein by reference. The non-porous phase is expected to provide a continuous surface for EC adhesion and spreading, mechanical strength, and elasticity to the scaffold. The porous phase will facilitate the 3-D growth of smooth muscle cells. Biphasic scaffolds were fabricated via the following procedures. Briefly, glass rods (~3 mm diameter) were coated with the pre-polymer solution and air dried to allow for solvent evaporation. Wall thickness of the tubes can be controlled by the number of coatings and the percent pre-polymer in the solution. The pre-coated pre-polymer was partially post-polymerized under 60° C. for 24 hr; the pre-polymer-coated glass rod is then inserted concentrically in a tubular mold that contains a salt/pre-polymer slurry. The pre-polymer/outer-mold/glass rod system is then placed in an oven for further post-polymerization. After salt-leaching, the biphasic scaffold was then de-molded from the glass rod and freeze dried. The resulting biphasic scaffold was stored in a desiccator before use. The same materials or different materials from the above family of elastomers can be utilized for both phases of the scaffold. Other biomedical materials widely used in current research and clinical application such as polylactide (PLA), polycaprolactone (PCL), poly(lactide-co-glycolide) (PLGA) may also be utilized for this novel scaffold design.

The thickness, degradation, and mechanical properties of inside non-porous phase can be well controlled by choosing various pre-polymers of this family of elastomers, pre-polymer concentration, coating times and post-polymerization conditions (burst pressure can be as high as 2800 mmHg). The degradable porous phase and non-porous phases are integrated since they are formed in-situ via post-polymerization. The cell culture experiments shown in FIG. 16 confirm that both HAEC and HASMC can attach and grow well in biphasic scaffolds. The results suggest that a biphasic scaffold design based on poly(diol citrate) is a viable strategy towards the engineering of small diameter blood vessels.

Synthesis of Poly(1,6-hexanediol-co-citric acid) (PHC)

In a typical experiment, 19.212 g citric acid and 11.817 g 1,6-hexanediol were added to a 250 ml three-neck round-bottom flask, fitted with an inlet adapter and an outlet adapter. The mixture was melted within 15 min by stirring at 160-165° C. in a silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for a predetermined time from one day to 3 weeks, depending on the temperature, to achieve the Poly(1,6-hexanediol-co-citric acid). Nitrogen was introduced into the reaction system before the polymer was taken out from the reaction system.

Synthesis of Poly(1,12-dodecanediol-co-citric acid) PDDC

In a typical experiment, 19.212 g citric acid and 20.234 g 1,12-dodecanediol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly(1,12-dodecanediol-co-citric acid). Nitrogen was introduced into the reaction system before the polymer was taken out from the reaction system.

Synthesis of Poly(1,8-octanediol-co-citric acid-co-glycerol)

In a typical experiment (Poly(1,8-octanediol-co-citric acid-co-1% glycerol), 23.0544 g citric acid, 16.5154 g 1,8-octanediol and 0.2167 g glycerol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for another hour at 140° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly(1,8-octanediol-co-citric acid-co-1% glycerol). Nitrogen was introduced into the reaction system before the polymer was taken out from the reaction system.

Synthesis of Poly(1,8-octanediol-citric acid-co-polyethylene oxide)

In a typical experiment, 38.424 g citric acid, 14.623 g 1,8-octanediol and 40 g polyethylene oxide with molecular weight 400 (PEO400)(100 g PEO1000 and 200 g PEO2000 respectively) (molar ratio: citric acid/1,8-octanediol/PEO400=1/0.5/0.5) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 135° C. The mixture was stirred for 2 hours at 135° C. to get the pre-polymer. Nitrogen was vented throughout the above procedures. The pre-polymer was post-polymerized at 120° C. under vacuum for predetermined time from one day to 3 days to achieve the Poly(1,8-octanediol-citric acid-co-polyethylene oxide). Nitrogen was introduced into the reaction system before the polymer was taken out from the reaction system. The molar ratios can be altered to achieve a series of polymers with different properties.

Synthesis of Poly(1,12-dodecanediol-citric acid-co-polyethylene oxide)

In a typical experiment, 38.424 g citric acid, 20.234 g 1,12-dodecanediol and 40 g polyethylene oxide with molecular weight 400 (PEO400)(100 g PEO1000 and 200 g PEO2000 respectively) (molar ratio: citric acid/1,8-octanediol/PEO400=1/0.5/0.5) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 120° C. under vacuum for predetermined time from one day to 3 days to achieve the Poly(1,12-dodecanediol-citric acid-co-polyethylene oxide). Nitrogen was introduced into the reaction system before the polymer was taken out from the reaction system. The molar ratios can be altered to achieve a series of polymers with different properties.

Synthesis of Poly(1,8-octanediol-citric acid-co-N-methyldiethanoamine) POCM.

In a typical experiment, 38.424 g citric acid, 26.321 g 1,8-octanediol and 2.3832 g N-methyldiethanoamine (MDEA) (molar ratio: citric acid/1,8-octanediol/MDEA=1/0.90/0.10) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 13520° C. The mixture was stirred for half an hour at 120° C. to get the pre-polymer. Nitrogen was vented throughout the above procedures. The pre-polymer was post-polymerized at 80° C. for 6 hours, 120° C. for 4 hours without vacuum and then 120° C. for 14 hours under vacuum to achieve the Poly(1,8-octanediol-citric acid-co-N-methyldiethanoamine). Nitrogen was introduced into the reaction system before the polymer was taken out from the reaction system. The molar ratios can be altered to citric acid/1,8-octanediol/MDEA=1/0.95/0.05.

Synthesis of Poly(1,12-dodecattediol-citric acid-co-N-methyldiethanoamine) PDDCM.

In a typical experiment, 38.424 g citric acid, 36.421 g 1,12-dodecanediol and 2.3832 g N-methyldiethanoamine (MDEA) (molar ratio: citric acid/1,8-octanediol/MDEA=1/0.90/0.10) were added to a 250 ml or 500 ml three-neck round-bottom flask, fitted with an inlet adapter and an outlet adapter. The mixture was melted within 15 min by stirring at 160-165° C. in a silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 80° C. for 6 hours, 120° C. for 4 hours without vacuum and then 120° C. for 14 hours under vacuum to achieve the Poly(1,12-dodecanediol-citric acid-co-N-methyldiethanoamine). Nitrogen was introduced into the reaction system before the polymer was taken out from the reaction system. The molar ratios can be altered to citric acid/1,12-dodecanediol/MDEA=1/0.95/0.05.

Example 2

Methods Employed in the Preparation and Characterization of the Grafts of the Invention Surface Modification of ePTFE Graft with POC:

Prior to modification, standard ePTFE grafts (Gore-Tex®, W.L. Gore & Associates Inc., Flagstaff Ariz., 6 mm inner diameter) were cleaned by first soaking under sonication in absolute ethanol then in acetone followed by vacuum drying. The lumen of ePTFE grafts were modified by mechanically coating a layer of POC through a spin-shearing method. Briefly, a 5 mm diameter glass rod was dipped into 10% of purified pre-POC solution in 1,4-dioxane and inserted horizontally into the motor of a mechanical stirrer (IKA®-Werke GMBH & CO. KG, Eurostar ST P CV PS S1, Staufen, Germany). The pre-polymer-coated glass rod was spun clockwise at 300 rpm for 2 minutes and a 6-cm-long piece of ePTFE graft was placed concentrically over the spinning rod. The lumen of the graft was sheared against the spinning rod for 2 minutes by manually rotating the graft counterclockwise. The above procedure was considered to be 1 coating. To change the amount of POC deposited onto the graft (and therefore the coating thickness), the above procedure was repeated 3, and 6 times (defined as 3 and 6 coatings) to assess POC coverage and effects on graft compliance with increasing polymer content. Followed by air-drying, the pre-POC coated ePTFE graft was put into an oven for 80° C., 2 days to obtain POC-ePTFE graft.

Characterization of POC-ePTFE Graft:

This Section details the characterization of exemplary coated implantable device materials prepared by the invention.

Fourier Transform Infrared (FTIR)) Analysis.

POC-ePTFE graft and control ePTFE graft were cut open into small piece (1×2 cm), modified side up, and placed on the sample stage of a FTIR spectrometer (Thermo Nicolet Nexus 870, Keck II, NUANCE, Northwestern University) under a mode of Diffuse reflectance infrared Fourier transform spectroscopy (DRIFTS) measurement, which is suited to characterize a rough surface.

X-Ray Photoelectron Spectroscopy (XPS) Analysis.

XPS spectra of the POC-ePTFE and untreated ePTFE graft (control) were acquired on an Omicron ESCA probe (electron spectroscopy for chemical analysis, Keck II, NUANCE, Northwestern University) at a power of 300 W. All measurements were taken under vacuum (<3×10−9 mbar).

Scanning Electron Microscopy (SEM).

The surface morphology of the lumen of POC-ePTFE and control grafts were sputter-coated with gold and examined under a SEM (Hitachi 3500N, EPIC, Northwestesrn Univeristy).

Contact Angle Measurements.

The water-in-air contact angles were measured at room temperature using the sessile drop method[20] using a Ramé-Hart goniometer and an imaging system (Ramé-Hart Inc., Mouttain Lake, N.J.) after placing water drops on the surfaces. The contact angles changes over time were monitored. Four independent measurements at different sites were averaged.

Compliance Measurements.

Compliance was defined as diameter changes percentage for a given pressure change, typically from 80 to 120 mmHg. Measurements were conducted on a custom-made in vitro closed-loop flow system. Computer controlled pressurization or a Harvard Apparatus pulsatile blood pump (Harvard Apparatus, Hollister, Mass.) was used to control pulsation frequency and pressure ranges. A LED micrometer (Keyence LS7000, Higashi-Yodogawa, Osaka) was used to non-invasively measure radial distension. The pressure and distension data over time was recorded with LabVIEW software (National Instruments, Austin Tex.).

Hemocompatibility Evaluation of POC-ePFE:

Platelet Adhesion:

The methods used to collect and prepare the platelets used in this study have been approved by the Institutional Review Board (IRB Project #1118-001) and the Office for the Protection of Research Subjects at Northwestern University. Blood was drawn from healthy adult volunteers by venipuncture into ACD anticoagulant (Acid Citrate Dextrose, Solution A; BD Franklin Lakes, N.J.). Platelet-Rich Plasma (PRP) was prepared as previously described (Grunkemeier, et al, 1998). Briefly, whole blood was centrifuged at 250 g for 15 minutes and the PRP removed. Plasma proteins were separated from the platelet fraction utilizing size exclusion chromatography. The columns (Bio-Rad, Hercules, Calif., #732-1010) were packed with Sepharose 2B (Sigma, St. Louis, Mo., #2B-300) and equilibrated with platelet-suspending buffer (PSB). The PRP was run though the column, to allow plasma proteins to bind to the sepharose. The platelet fraction was collected, counted, and adjusted to a final concentration of 5×10$^7$/mL in PSB. Test and control samples were incubated with PRP for 1 hour at 37° C. under static conditions. The suspension was aspirated and each well rinsed carefully six times with PBS. The number of adherent platelets was determined by detecting the amount of lactate dehydrogenase (LDH) using a modification of the methods described by Tamada et al[30]. Adherent platelets were lysed by incubation with Triton-PSB buffer at 37° C. for 30 minutes. A colorimetric substrate for LDH (Roche Diagnostics Corporation, Indianapolis, Ind., 1644793) was added to the solution and incubated for 20 minutes at 37° C. The reaction was stopped by the addition of 1N HCl. The O.D. was read at 490 nm with reference wavelength of 650. Test and control samples were incubated with the PRP for 1 hour at 37° C. under static conditions. Following incubation, the suspension was aspirated and each well was rinsed carefully six times with PBS. Adherent platelets were fixed using 2.5% glutaraldehyde in PBS for at least 2 hours, dehydrated in a graded series of ethanol and critical point dried. The samples were then sputter coated with a 7 nm layer of gold and observed using SEM.

Platelet Activation:

Test and control samples were incubated with whole blood for 1 hour at 37° C. under static conditions. The blood was removed and centrifuged at 2000 g for 10 minutes to obtain the Platelet Poor Plasma (PPP). Soluble P-selectin levels in the plasma were determined using an ELISA kit (Parameter Human soluble P-selectin Immunoassay, R & D Systems, Minneapolis, Minn., #BBE 6).

Aortoiliac Bypass Graft Model in Pigs:

All procedures and care were performed in accordance with the regulations of the animal care and use committee of Northwestern University. Three male pigs (Yorkshire Landrace, Oak Hill Genetics, Fanning Farms) weighing 20 to 25 Kg were used in the study. The animals received pre-operative analgesia with buprenorphine (0.05 mg/kg IM), and sedation with Acepromazine (0.15 mg/kg IM) and Ketamine (20 mg/kg IM). After intubation, maintenance anesthesia was conducted with Isoflurane (0.5-2.0%) delivered with 100% oxygen. A midline abdominal incision was made in order to expose and dissect both iliac arteries. Prior to vascular occlusion, the animals received intravenous heparin (150 units/kg). Bilateral aortoiliac bypass grafting was performed with a POC-ePTFE graft on one side and an untreated ePTFE graft (control) on the contralateral side. All animals received aspirin (325 mg daily) as an antiplatelet therapy pre and postoperatively. Animals were monitored for the patency of the grafts via MRI at CAMRI (Center for Advanced MRI, Northwestern University). Contrast enhanced MR was performed using a time-resolved T1-wieghted gradient echo pulse sequence. A time-series of 3D contrast-enhanced MR angiograms were acquired with an injection of 0.1 mmol/kg of a gadolinium based contrast agent (Magnevist, Berlex, Princeton, N.J.). Following completion of the angiogram, the bypass grafts was harvested for further analysis via histology and immunohistochemistry.

Histology and Immunohistochemistry Staining of the Grafts:

Grafts and adjacent 3-cm segments of attached vessel at each anastomosis were harvested and fixed in 10% neutral buffered formalin (Sigma, Milwaukee, Wis.). Sections of each graft were also fixed in a 2.5% glutaraldehyde solution for observation via SEM. Formalin-fixed grafts were embedded in paraffin and sectioned at a distance of 2 mm from the proximal and distal anastomoses. Five-micron sections were cut and stained with hematoxylin-eosin (H&E) staining, and macrophage staining using MAC387 antibody (Serotec, UK).

Seeding of Endothelial Progenitor Cells on POC-ePTFE Grafts:

Prior to cell seeding, pig endothelial progenitor cells (EPCs) isolated from peripheral blood of pigs were stained with vWF (von Willerbrand Factor) to confirm their endothelial phenotype. POC-ePTFE and untreated ePTFE grafts (6 cm in length) were gas-sterilized via exposure to ethylene oxide and placed in a culture dish (150×15 mm, Becton Dickinson, N.Y.). An suspension of EPCs was injected into the lumen of the grafts at a density of $3.9 \times 0^6$ cells/ml and incubated at 37° C. for 60 min. The graft was rotated 180°, and an additional suspension of EPCs injected into the lumen of the grafts. The cell suspension was incubated in the grafts for 60 min prior to adding 80 ml of fresh culture medium to the each culture dish. After culture for 1 week, grafts were taken out of culture dishes and washed with PBS three times. Thereafter the grafts were cut into three 2 cm-long segments. Each segment was subsequently cut into two parts. One was fixed with 2.5% glutaraldehyde in PBS for observation via SEM and the other part was fixed with 10% neutral buffered formalin for H&E staining and vWF (von Willerbrand Factor) staining.

Example 2

Results and Discussion ePTFE grafts are manufactured by a heating, extruding, and longitudinal stretching at a high strain rate and cracking into a non-woven porous tube. ePTFE grafts are characteristic of a node-fibril structure (FIG. 1A) in which non-continuous nodes connect through fine fibrils. Average internodal distance is about 30 μm for standard ePTFE grafts. ePTFE grafts trigger inflammation, thrombosis and incomplete endothelium formation, the major causes for graft failure together with the compliance mismatch. Many attempts have been tried to modify the lumen of ePTFE grafts to abolish their anti-adhesion properties and improve endothelialization including carbon coating to increase surface electronegativity for reduced thrombus formation[31, 32], and attaching anticoagulant or antithrombotic agents to the grafts[15, 33, 34 13-17] through chemical or physical modifications. However, there are still no satisfactory grafts with a long term patency available, especially for small diameter blood vessel replacements that are associated with problems caused by unsatisfactory antithrombogenicity, weak endothelial adherence, and always even worse compliance mismatch after modification[13, 35-38].

Figures 2A, 2B, 2C, 2D:
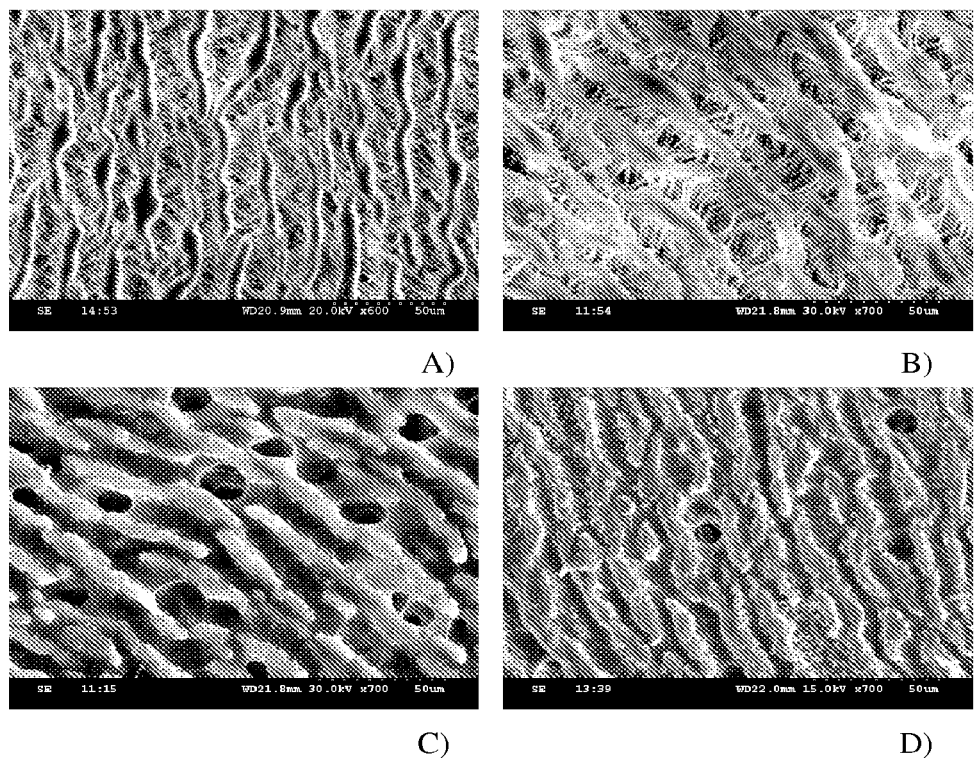
FIG. 2 shows SEM images of the graft lumen. A) untreated ePTFE graft; B) POC-ePTFE graft with 1 POC coating (POC-ePTFE 1C); C) POC-ePTFE graft with 3 coatings (POC-ePTFE 3C); D) POC-ePTFE graft with 6 coatings (POC-ePTFE 6C). Scale bar=50 μm.

Using a newly developed biodegradable elastomer, the lumen of ePTFE grafts have been modified via a convenient mechanical spin-shearing method. FIGS. 1B, C and D showed the morphology of ePTFE lumen after different times of coating with biodegradable elastomeric POC. The more times the coating was applied, the higher was the coverage of POC coating on ePTFE lumen. Notably, this elastic coating could maintain the aligned structure of fibril between nodes instead of binding the fibrils together when using other non-elastic polyers such as poly(ethyleneimide) (PEI, data not shown here). Thus, it is understandable that the coated ePTFE grafts could maintain their original size instead of shrinking as can happen when using other non-elastic polymers. The elastic coating is expected to expand or contract with the nodes and fibrils under the dynamic physiological fluid flow. The compliance measurements (FIG. 2) on modified ePTFE grafts confirmed that with limited coating (<3 times under the proposed coating conditions) the compliance of the ePTFE grafts were not adversely affected (POC-ePTFE 1C and POC-ePTFE 3C vs. control ePTFE, $P<0.05$).

Surface characterization of ePTFE grafts through surface FTIR analysis and surface element composition analysis (XPS) confirmed the successful coating of POC on ePTFE grafts. FIG. 3 showed that the broad peaks centered at 3475 and 3215 $cm^{-1}$, peaks at 2925 and 2850 $cm^{-1}$, and peaks within 1690 to 1750 $cm^{-1}$ in spectra B were assigned to the hydroxyl group stretching vibration and $\upsilon_{O-H}$ of carboxyl groups, the —CH2— groups, and carbonyl (C=O) groups from POC.[28] XPS analysis showed the F/C of control ePTFE was 2.1 which was exactly in agreement with the previous work[16]. There is a peak appearing at approximately 539 ev, which is assigned to O1s from POC. A decreased F/C (1.36) in POC-ePTFE occurred with an increased O/C from 0 to 0.13 compared with control ePTFE.

FIG. 5 showed that the initial contact angle of ePTFE was 132.5±0.2°. Introduction of POC on ePTFE could significantly decrease the initial contact angles to 121.2±0.2°. More importantly, The equilibrium water-in-air contact angles of POC-ePTFE after 75 min of contact time could reach 38.1±3.9° as compared to 101.7±0.8° of control ePTFE suggesting that POC-ePTFE have very good wettability, which is expected to facilitate the cell adhesion.[19]

Figure 7:
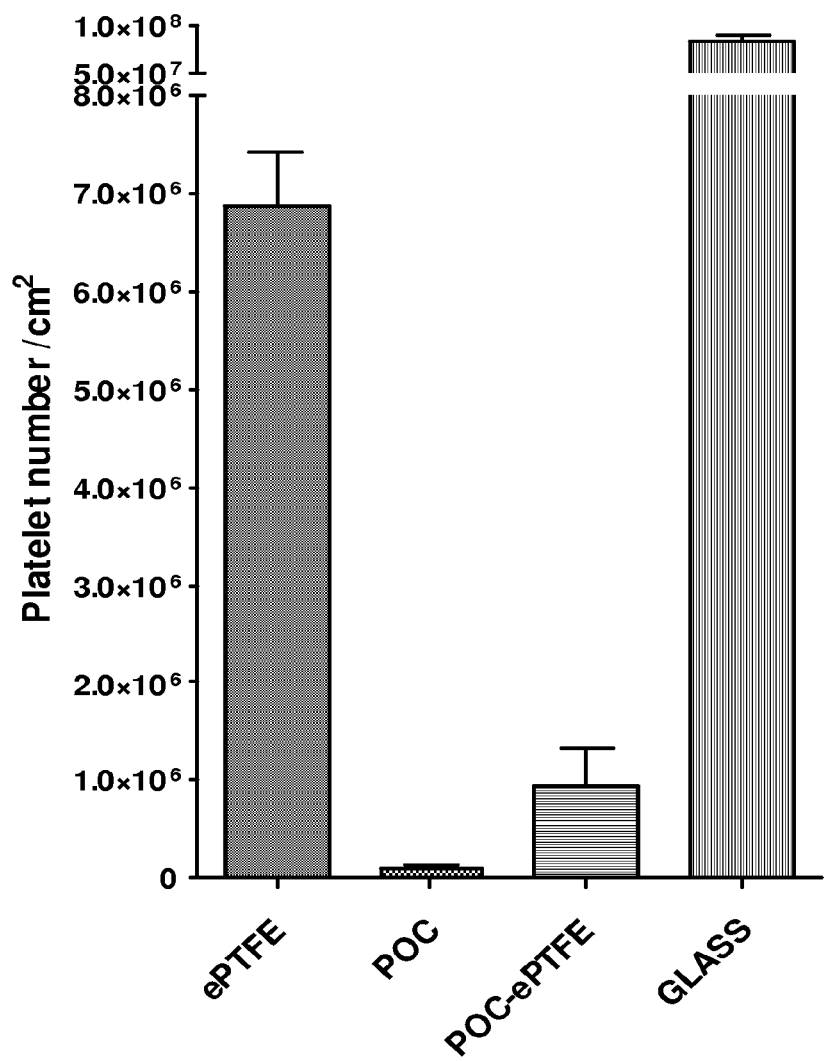
FIG. 7 shows a comparison of Platelet adhesion on various type of materials.

Coating an ePTFE graft with POC could drastically improve the hemocompatibility of ePTFE grafts. FIG. 6 showed the comparision of platelet adhesion on various type of materials. POC could significantly inhibit the platelet adhesion. Since ePTFE is not a transparent material, the clotting assay was only conducted on POC films as compared with TCP and PLGA. The results of the clotting assay (FIG. 7) suggested that clotting time could be significantly delayed by coating the ePTFE graft with POC. Interestingly, the clotting delay of POC is significantly longer than the commercially available biodegradable polymer, PLGA, which is widely used in tissue engineering.

Figure 8:
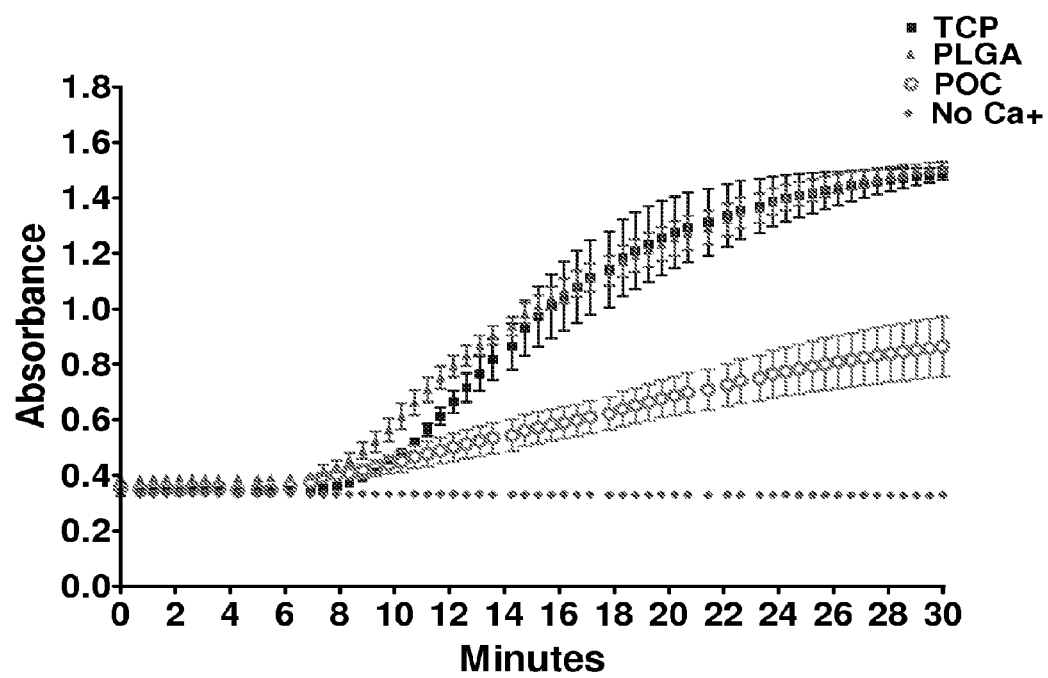
FIG. 8 shows a plasma re-calcification clotting profiles. Platelet poor plasma on TCP (blue), PLGA (80:20)(red), and POC (green). Clotting is significantly delayed on POC relative to TCP and PLGA. Purple marks are PPP on TCP with no calcium. Mean±S.D., N=5.

The in vivo biocompatibility of POC-ePTFE grafts was evaluated through a pig iliac artery model. Grafts were explanted after 1 week implantation. FIGS. 8A and B showed that both POC-ePTFE and control grafts were open in 3 pigs after 1 week implantation. Inflammation cells staining (MAC 387) indicated there are less recruited macrophages in POC-ePTFE grafts compared to control grafts (FIGS. 8C and D). SEM pictures (FIGS. 8E and F) indicated that the lumen of POC-ePTFE has less fibrin coagulum, amorphous platelet-rich and/or white blood cell-rich materials development compared to control ePTFE. The above results demonstrated the biocompatibility and hemocompatibility of ePTFE grafts were greatly improved with POC coating.

As for the issue of cell sources, harvesting autologous endothelial cells remains a challenge since the ECs are normally harvested by sacrificing a healthy blood vessel. Recent studies evidenced that matures ECs and immature endothelial-like cells float in the peripheral blood[39-41]. Yamashita has reported embryonic vascular progenitors capable of differentiating into both endothelial and smooth muscle-like cells in response to different culturing environment.[42] Thus, there is interest in using autologous EPCs isolated from pig peripheral blood to seed the grafts for a pig model. FIG. 9 showed the SEM observation of EPCs seeded grafts. EPCs appeared as patches on control grafts suggesting an incomplete endothelialization while a totally confluent endothelium was formed on POC-ePTFE. This indicated that POC-ePTFE could facilitate the formation of complete endothelialization. ECs have been confirmed to be able to lay down extracellular matrix (ECM)[8, 9].

Thus, a tissue-engineered endothelium could be formed, which is expected to be much better than the endothelium formed using current methods. Firstly, the POC coating provides an excellent support for ECs adhesion; Secondly, since POC is a biodegradable polymer, the degrading POC will gradually be replaced by the ECM produced by ECs; Thirdly, this gradual replacement is expected to ensure the maintenance of a complete endothelium. Given that the POC coating is wrapping around the fibrils of the ePTFE lumen just like the fibrils inserted in the POC films, the ECM produced by ECs could be induced by the gradual degradation of POC and wrap around the fibrils eventually. This kind of ECM support would be ideal for effectively supporting an endothelium.

In conclusion, the present study has for the first time demonstrated the use of a novel biodegradable elastomeric polymer to modify the ePTFE graft via a convenient method to tissue engineer an endothelium. The long term patency of ePTFE grafts is expected to be greatly improved. The in vivo long term evaluation of POC-ePTFE is underway.

REFERENCES

The following references are referred to herein throughout using a numeric identifier. Each of these references is incorporated herein by reference in its entirety.

[1] Heart disease and stroke statistics update. American Heart Association 2005.
[2] Tiwari A, Salacinski H, Seifalian A M, Hamilton G. New prostheses for use in bypass grafts with special emphasis on polyurethanes. Cardiovascular Surgery 2002; 10:191-197.
[3] Bezuidenhout D, Zilla P, Vascular grafts, in: Wnek G E and Bowlin G L, editors. Encyclopedia of Biomaterials and Biomedical Engineering. Marcel Dekker; 2004. p.
[4] Nerem R M, Seliktar D. Vascular tissue engineering. Annu Rev Biomed Eng 2001; 3:225-243.
[5] Niklason L E, Gao J, Abbott W M, Hirschi K K, Houser S, Marini R, Langer R. Functional arteries grown in vitro. Science 1999; 284:489.
[6] L'Heureux N, Paquet S, Labbe R, Germain L, Auger F A. A completely biological tissue-engineered human blood vessel. FASEB J 1998; 12:47-56.
[7] Kakisis J D, Liapis C D, Breuer C, Sumpio B E. Artificial blood vessel: The Holy Grail of peripheral vascular surgery. J Vasc Surg 2005; 41:349-354.
[8] Vlodaysky I, Folkman J, Sullivan R, Fridman R, Ishai-Michaeli R, Sasse J, Klagsbrun M. Endothelial cell-derived basic fibroblast growth factor: Synthesis and deposition into subendothelial extracellular matrix. Proc Natl Acad Sci USA 1987; 84:2292-2296.
[9] Gospodarowicz D, III C. Extracellular matrix and control of proliferation of vascular endothelial cells. J Clin Invest 1980; 65:1351-1364.
[10] Xue L, Greisler H P. Biomaterials in the development and future of vascular grafts. J Vasc Surg 2003; 37:472-480.
[11] Niklason L E, Langer R S. Advances in tissue engineering of blood vessels and other tissues. Transpl Immunol 1997; 5:303-306.
[12] Salacinski H J, Tiwari A, Hamilton G, Seifalian A M. Cellular engineering of vascular bypass grafts: role of chemical coatings for enhancing endothelial cell attachment. Med Biol Eng COmput 2001; 39:609-618.
[13] Seifalian A M, Tiwari A, Hamilton G, Salacinski H J. Improving the clinical patency of prosthetic vascular and coronary bypass grafts: the role of seeding and tissue engineering. Artif Organs 2002; 26:307-320.
[14] Li J, Singh M J, Nelson P R, Hendricks G M, Itani M, Rohrer M J, Cutler B S. Immobilization of human thrombomodulin to expeander polytetrafluoroethylene. Journal of Surgical Research 2002; 105:200-208.
[15] Lin P H, Chen C, Bush R L, Yao Q, Lumsden A B, Hanson S R. Small-caliber heparin-coated ePTFE grafts reduce platelet deposition and neointimal hyperplasia in a baboon model. J Vasc Surg 2004; 39:1322-1328.

[16] Noh I, Goodman S L, Hubbell J A. Chemical modification and photograft polymerization upon expanded poly(tetrafluoroethylene). J Biomater Sci Polymer Edn 1998; 9:407-426.

[17] Guan J, Sacks M S, Beckman E J, Wagner W R. Biodegradable poly(ether ester urethane)urea elastomers based on poly(ether ester) triblock copolymers and putrescine: synthesis, characterization and cytocompatibility. Biomaterials 2004; 25:85-96.

[18] Tseng D Y, Edelman E R. Effects of amide and amine plasma-treated ePTFE vascular grafts on endothelial cell lining in an artificial circulatory system. J Biomed Mater Res 1998; 42:188-198.

[19] Yang J, Wan Y, Yang J, Bei J, Wang S. Plasma-treated, collagen-anchored polylactones: its cell affinity evaluation under shear or shear-free conditions. J Biomed Mater Res 2003; 67:1139-1147.

[20] Yang J, Bei J, Wang S. Enhanced cell affinity of poly(D,L-lactide) by combining plasma treatment with collagen anchorage. Biomaterials 2002; 23:2607-2614.

[21] Yang J, Bei J, Wang S. Improving cell affinity of poly(D,L-lactide) film modified by anhydrous ammonia plasma treatment. Polym Adv Technol 2002; 13:220-226.

[22] Yang J, Shi G X, Bei J Z, Wang S G, Cao Y L, Shang Q X, Yang G H, Wang W J. Fabrication and surface modification of macroporous Poly(L-lactic acid) and Poly(L-lactic-co-glycolic acid)(70/30) cells scaffold for human skin fibroblast cells culture. J. Biomed. Mater. Res. 2002; 62:438-446.

[23] Wan Y, Yang J, Yang J, Bei J, Wang S. Cell adhesion on gaseous plasma modified poly(L-lactide) surface under shear stress field. Biomaterials 2003; 24:3757-3764.

[24] Chen_Yang Y W, Chen C W, Tseng S C, Huang J, Wu Y Z. Surface modification of bi-axially expanded poly(tetrafluoroethylene) by plasma polymerization of ethylene. Surface and Coating Technology 2004; 176:148-156.

[25] Seifalian A M, Tiwari A, Hamilton G, Salacinski H J. Improving the clinical patency of prosthetic vascular and coronary bypass grafts: the role of seeding and tissue engineering. Artif Organs 2001; 26:307-320.

[26] Yang J, Webb A R, Ameer G A. Novel citric acid-based biodegradable elastomers for tissue engineering. Adv Mater 2004; 16:511-516.

[27] Kang Y, Yang J, Khan S, Anissian L, Ameer G A. A novel biodegradable elastomer for cartilage tissue engineering. J Biomed Mater Res 2006; in press.

[28] Yang J, Webb A R, Pickerill S J, Hageman G, Ameer G A. Synthesis and evaluation of poly(diol citrates) biodegradable elastomers. Biomaterials 2006:(in press).

[29] Yang J, Webb A R, Ameer G A, Biodegradable elastomeric polymers for tissue engineering, in: Mallapragada S K and Narasimhan B, editors. Handbood of biodegradable polymeric materials and their applications. American Scientific Publishers; 2005. p. 191-232.

[30] Tamada Y, Kulik E A, Ikada Y. Simple method for platelet counting. Biomaterials 1995; 16:259-261.

[31] Akers D L, Du Y H, Kempczinski R F. The effect of carbon coating and porosity on early patency of expanded polytetrafluoroethylene grafts: an experimental study. J Vasc Surg 1993; 18:10-15.

[32] Tsuchida H, Cameron B L, Marcus C S, Wilson S E. Modified polytetrafluoroethylene: indium 111-labeled platelet deposition on carbon-lined and high-porosity polytetrafluoroethylene grafts. J Vasc Surg 1992; 16:643-649; discussion 649-650.

[33] Chen C, Ofenloch J C, Yianni Y P, Hanson S R, Lumsden A B. Phosphorylcholine coating of ePTFE reduces platelet deposition and neointimal hyperplasia in arteriovenous grafts. J Surg Res 1998; 77:119-125.

[34] Zhang Q, Wang C, Babukutty Y, Ohyama T, Kogoma M, Kodama M. Biocompatibility evaluation of ePTFE membrane modified with PEG in atmospheric pressure glow discharge. J Biomed Mater Res 2002; 60:502-509.

[35] Kannan R Y, Salacinski H J, Butler P E, Hamilton G, Scifalian A M. Current status of prosthetic bypass grafts: a review. J Biomed Mater Res Part B: Appl Biomater 2005; 74B:570-581.

[36] van der Zijpp Y J, Poot A A, Feijen J. Endothelialization of small-diameter vascular prostheses. Arch Physiol Biochem 2003; 111:415-427.

[37] Bos G W, Poot A A, Beugeling T, van Aken W G, Feijen J. Small-diameter vascular graft prostheses: current status. Arch Physiol Biochem 1998; 106:100-115.

[38] Teebken O E, Haverich A. Tissue engineering of small diameter vascular grafts. Eur J Vasc Endovasc Surg 2002; 23:475-485.

[39] Asahara T, Murohara T, Sullivan A, Silver M, van der Zee R, Li T, Witzenbichler B, Schatteman G, Isner J M. Isolation of putative progenitor endothelial cells for angiogenesis. Science 1997; 275:964-967.

[40] Shi Q, Rafii S, Wu M H, Wijelath E S, Yu C, Ishida A, Fujita Y, Kothari S, Mohle R, Sauvage L R, Moore M A, Storb R F, Hammond W P. Evidence for circulating bone marrow-derived endothelial cells. Blood 1998; 92:362-367.

[41] Peichev M, Naiyer A J, Pereira D, Zhu Z, Lane W J, Williams M, Oz M C, Hicklin D J, Witte L, Moore M A, Rafii S. Expression of VEGFR-2 and AC133 by circulating human CD34(+) cells identifies a population of functional endothelial precursors. Blood 2000; 95:952-958.

[42] Yamashita J, Itoh H, Hirashima M. Flk1-positive cells derived from embryonic stem cells serve as vascular progenitors. Nature 2000; 408:92-96.

We claim:

1. An implantable medical device, wherein at least one surface of said device comprises a polyester of a linear aliphatic diol monomer and a citric acid monomer, said polyester having ascorbic acid covalently bound thereto.

2. The composition of claim 1, wherein the linear aliphatic diol monomer comprises between 2 and 20 carbons.

3. The composition of claim 2, wherein the linear aliphatic diol monomer is selected from the list consisting of 1,8-octanediol, 1,10-decanediol, and 1,12-dodecanediol.

4. The composition of claim 3, wherein the linear aliphatic diol monomer comprises 1,8-octanediol.

5. The composition of claim 1, wherein said polyester is biodegradeable.

6. The composition of claim 1, wherein said polyester is biocompatable.

7. The composition of claim 1, wherein said polyester is produced by polycondensation of citric acid with linear aliphatic dihydroxy monomers.

8. The implantable medical device of claim 1, wherein said base material is selected from the group consisting of: stainless steel, tantalum, titanium, nitinol, gold, platinum, inconel, iridium, silver, tungsten, carbon, carbon fiber, cellulose acetate, cellulose nitrate, silicone, polyethylene terephthalate, polyurethane, polyamide, polyester, polyorthoester, polyanhydride, polyether sulfone, polycarbonate, polypropylene, polytetrafluoroethylene, polylactic acid, polyglycolic acid, a polyanhydride, polycaprolactone, polyhydroxybutyrate valerate, a protein, an extracellular matrix component, collagen, fibrin, polyethylene, or a suitable mixture, copolymer, or alloy of any of the above.

9. The implantable medical device of claim 1, wherein said base material is expanded polytetrafluorotethylene.

10. The implantable medical device of claim 1, wherein the polyester is impregnated with one or more therapeutic agents and/or cells.

11. The implantable medical device of claim 10, wherein said therapeutic agent is selected from the group consisting of an antisense nucleotide, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antimicrobial agent, an antibiotic, an antiplatelet agent, an antimitotic, a microtubule inhibitor, an actin inhibitor, a remodeling inhibitor, an agent for molecular genetic intervention, a cell cycle inhibitor, an inhibitor of the surface glycoprotein receptor, an antimetabolite, an antiproliferative agent, an anti-cancer chemotherapeutic agent, an anti-inflammatory steroid, an immunosuppressive agent, an antibiotic, a radiotherapeutic agent, iodine-containing compounds, barium-containing compounds, a heavy metal functioning as a radiopaque agent, a peptide, a protein, an enzyme, an extracellular matrix component, a cellular component, an angiotensin converting enzyme (ACE) inhibitor, ascorbic acid, a free radical scavenger, an iron chelator, an antioxidant, or a mixture of any of the above.

12. The implantable medical device of claim 11, wherein said therapeutic agent is a nitric oxide promoter.

13. The implantable medical device of claim 11, wherein said therapeutic agent is an anti-inflammatory agent.

14. The implantable medical device of claim 1, wherein said device is a blood vessel graft.

* * * * *

UNITED STATES PATENT AND TRADEMARK OFFICE
CERTIFICATE OF CORRECTION

PATENT NO. : 8,758,796 B2  
APPLICATION NO. : 13/848339  
DATED : June 24, 2014  
INVENTOR(S) : Guillermo Ameer, Jian Yang and Melina Kibbe It is certified that error appears in the above-identified patent and that said Letters Patent is hereby corrected as shown below:

In the Claims:

Column 26, lines 38 to 41, should read:

An implantable medical device, wherein the medical device comprises a base material and a coating, wherein the coating comprises a polyester of a linear aliphatic diol monomer and a citric acid monomer and wherein ascorbic acid is covalently bound to the surface of the polyester.

Signed and Sealed this  
Ninth Day of September, 2014

Michelle K. Lee  
*Deputy Director of the United States Patent and Trademark Office*